US011629381B2

(12) United States Patent
Tsao et al.

(10) Patent No.: US 11,629,381 B2
(45) Date of Patent: Apr. 18, 2023

(54) QUALITY CONTROL TEMPLATES ENSURING VALIDITY OF SEQUENCING-BASED ASSAYS

(71) Applicant: BillionToOne, Inc., Palo Alto, CA (US)

(72) Inventors: David Tsao, Palo Alto, CA (US); Sukrit Silas, Palo Alto, CA (US); Oguzhan Atay, Palo Alto, CA (US)

(73) Assignee: BILLIONTOONE, INC., Palo Alto, CA (US)

( * ) Notice: Subject to any disclaimer, the term of this patent is extended or adjusted under 35 U.S.C. 154(b) by 1291 days.

(21) Appl. No.: 16/056,254

(22) Filed: Aug. 6, 2018

(65) Prior Publication Data

US 2019/0211395 A1 Jul. 11, 2019

Related U.S. Application Data

(60) Provisional application No. 62/614,236, filed on Jan. 5, 2018.

(51) Int. Cl.
| | | |
|---|---|---|
| *C12Q 1/6876* | (2018.01) | |
| *C12Q 1/6869* | (2018.01) | |
| *G16B 30/00* | (2019.01) | |
| *G16B 20/00* | (2019.01) | |
| *G16B 40/30* | (2019.01) | |
| *G16B 20/10* | (2019.01) | |
| *G16H 50/20* | (2018.01) | |
| *C40B 40/06* | (2006.01) | |
| *C40B 70/00* | (2006.01) | |

(52) U.S. Cl.
CPC ......... *C12Q 1/6876* (2013.01); *C12Q 1/6869* (2013.01); *G16B 20/00* (2019.02); *G16B 20/10* (2019.02); *G16B 30/00* (2019.02); *G16B 40/30* (2019.02); *C12Q 2600/112* (2013.01); *C12Q 2600/156* (2013.01); *C12Q 2600/166* (2013.01); *C40B 40/06* (2013.01); *C40B 70/00* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 8,195,415 | B2 | 6/2012 | Fan et al. |
| 8,467,976 | B2 | 6/2013 | Lo et al. |
| 8,688,388 | B2 | 4/2014 | Dzakula et al. |
| 8,706,422 | B2 | 4/2014 | Lo et al. |
| 8,877,442 | B2 | 11/2014 | Quake et al. |
| 9,512,480 | B2 | 12/2016 | Lo et al. |
| 9,944,973 | B2 | 4/2018 | Willey et al. |
| 2007/0009884 | A1 | 1/2007 | Stoughton et al. |
| 2007/0092869 | A1 | 4/2007 | Fulmer-Smentek et al. |
| 2008/0124712 | A1 | 5/2008 | Hantash et al. |
| 2010/0323352 | A1 | 12/2010 | Lo et al. |
| 2011/0033861 | A1 | 2/2011 | Wu et al. |
| 2011/0201507 | A1 | 8/2011 | Rava et al. |
| 2012/0021919 | A1 | 1/2012 | Scholl et al. |
| 2012/0270739 | A1 | 10/2012 | Rava et al. |
| 2013/0022973 | A1 | 1/2013 | Hansen et al. |
| 2013/0130923 | A1 | 5/2013 | Ehrich et al. |
| 2014/0195164 | A1 | 7/2014 | Lo et al. |
| 2015/0099266 | A1 | 4/2015 | Samuels et al. |
| 2015/0133391 | A1 | 5/2015 | De Vlaminick et al. |
| 2015/0152474 | A1 | 6/2015 | Pawlowski et al. |
| 2015/0284783 | A1 | 10/2015 | Canton |
| 2016/0040229 | A1 | 2/2016 | Talasaz et al. |
| 2016/0130649 | A1 | 5/2016 | Xie et al. |
| 2016/0222391 | A1 | 8/2016 | Krieg et al. |
| 2016/0251719 | A1 | 9/2016 | Umbarger |
| 2016/0319345 | A1 | 11/2016 | Gnerre et al. |
| 2017/0175187 | A1 | 6/2017 | Rabinowitz et al. |
| 2017/0275691 | A1 | 9/2017 | Karius et al. |
| 2017/0327869 | A1 | 11/2017 | Schutz et al. |
| 2018/0023125 | A1 | 1/2018 | Talasaz et al. |

FOREIGN PATENT DOCUMENTS

| | | |
|---|---|---|
| JP | 2013-530727 A | 8/2013 |
| JP | 2014-520509 A | 8/2014 |
| JP | 2015-521482 A | 7/2015 |
| WO | 2011091046 A1 | 7/2011 |
| WO | 2011156795 A2 | 12/2011 |
| WO | 2012058316 A1 | 5/2012 |
| WO | 2012129363 A2 | 9/2012 |

(Continued)

OTHER PUBLICATIONS

Tourlousse et al., "Synthetic spike-in standards for high-throughput 16S rRNA gene amplicon sequencing," Nucleic Acids Res. 2017, 45(4):e23, published online Dec. 15, 2016. (Year: 2016).*

Japan Patent Office, Office Action, JP Patent Application No. 2020-537213, dated Aug. 17, 2021, ten pages.

Tourlousse, D.M. et al., "Synthetic spike-in standards for high-throughput 16S rRNA gene amplicon sequencing," Nucleic Acids Research, vol. 45, No. 4, e23, Dec. 15, 2016, pp. 1-14 and supplementary data.

Applied Biosystems, Application Note: Detection and Quantification of Sequence Variants from Sanger Sequencing 1 Traces, Determination of minor alleles by analyzing peak height dat. Retrieved from the internet:<URL: http://www.nstillcase.com/Downloads/seq-quantification-app-note.pdf>.

(Continued)

*Primary Examiner* — Kaijiang Zhang

(74) *Attorney, Agent, or Firm* — Fenwick & West LLP

(57) ABSTRACT

Embodiments of a method and/or system can include generating a set of quality control template (QCT) molecules; determining a set of QCT sequence read clusters based on the set of QCT molecules, such as based on variation regions of the set of QCT molecules; and based on the set of QCT sequence read clusters, determining a sequencing-related parameter, such as a contamination parameter and/or molecule count parameter, associated with the at least one of sequencing library preparation and sequencing.

17 Claims, 21 Drawing Sheets

(56) References Cited

FOREIGN PATENT DOCUMENTS

| WO | 2014039556 A1 | 3/2014 |
|---|---|---|
| WO | 2014082032 A1 | 5/2014 |
| WO | 2017165864 A1 | 9/2017 |
| WO | 2017210372 A1 | 12/2017 |
| WO | 2018031486 A1 | 2/2018 |
| WO | 2014127484 A1 | 11/2018 |
| WO | WO 2019/028462 A1 | 2/2019 |

OTHER PUBLICATIONS

Darr, I. M., et al., "Inferring relative proportions of DNA variants from sequencing electropherograms", Bioinformatics, vol. 25, Issue 24, hllps://doi.org/10.1093/bioinformatics/btp583,Oct. 9, 2009, 3244-3250.

Curci, Pasquale Luca, et al., "How a Small Double-Stranded Trick Can Mislead Sanger Sequencing", J Biomol Tech. vol. 26, Issue 3, Sep. 1, 2015, 80-82.

International Search Report and the Written Opinion of the International Searching Authority, Application No. PCT/US18/45419, dated Dec. 21, 2018.

International Search Report and Written Opinion for PCT Application No. PCT/US2018/045394 dated Oct. 10, 2018.

International Search Report and the Written Opinion, Application No. PCT/US19/014340, dated Mar. 29, 2019.

Kaboev, O. K., et al., "PCR hot start using primers with the structure of molecular beacons {hairpin-like structure)", Nucl Acids Res, Sep. 12, 2000, vol. 28, No. 21.

Tourlousse, Dieter M., et al., "Synthetic spike-in standards for high-throughput 16S rRNA gene amplicon 4 sequencing", Biomedical Research Institute, National Institute of Advanced Industrial Science and Technology, Dec. 15, 2016.

Yan, Ti-Zhen, et al., "Reliable Detection of Paternal SNPs within Deletion Breakpoints for Non-Invasive Prenatal 2 Exclusion of Homozygous a-Thalassemia in Meternal Plasma", PLoS One, Sep. 29, 2011, vol. 6, No. 9, e24779, pp. 1-9.

International Search Report and Written Opinion for PCT Application No. PCT/US2018/045434 dated Nov. 29, 2018.

European Patent Office, Extended European Search Report and Opinion, EP Patent Application No. 18898428.0, dated Sep. 27, 2021, eight pages.

IP Australia, Examination report No. 1, AU Patent Application No. 2018399524, dated Nov. 8, 2021, four pages.

International Search Report and the Written Opinion, Application No. PCT/US19/45331, dated Oct. 25, 2019.

Tsao, et al. "A novel high-throughput molecular counting method with single base-pair resolution enables accurate single-gene NIPT," bioRxiv, Apr. 3, 2019 (Apr. 3, 2019), pp. 1-20.

Lun, Fiona M.F., et al., "Noninvasive prenatal diagnosis of monogenic diseases by digital size selection and relative mutation dosage on DNA in maternal plasma.", PNAS vol. 105, Dec. 16, 2008, 19920-19925.

Quail, M. A., et al., "SASI-Seq: sample assurance Spike-Ins, and highly differentiating 384 barcoding for Illumina sequencing.", BMC Genomics, 2014, 1-12.

Silas, S. , et al., "Direct CRISPR spacer acquisition from RNA by a natural reverse transcriptase-Cas1 fusion protein.", Science, Feb. 26, 2016, 1-31.

Sinha, R., et al., "Index Switching Causes "Spreading-Of-Signal" Among Multiplexed Samples In Illumina HiSeq 4000 DNA Sequencing.", Apr. 9, 2017, 1-29.

International Preliminary Report on Patentability for PCT/US2018/045394, dated Feb. 4, 2020.

International Preliminary Report on Patentability for PCT/US2018/045419 dated Feb. 4, 2020.

* cited by examiner

| | sample_id | num_seqs | | contam_frac | collision_frac | contam_collision_frac | | ident_frac | | reads_per_qctmol | |
|---|---|---|---|---|---|---|---|---|---|---|---|
| X | A01 | X | 8 | 0.633 | 0.000 | X | 0.633 | X | 0.721 | X | 2.5 |
| X | A02 | ✓ | 151 | 0.048 | 0.029 | X | 0.078 | X | 0.946 | X | 21.9 |
| X | A03 | X | 45 | 0.033 | 0.607 | X | 0.640 | ✓ | 0.968 | X | 27.2 |
| X | A04 | X | 45 | 0.086 | 0.403 | X | 0.488 | X | 0.594 | X | 9.2 |
| X | A05 | ✓ | 263 | 0.005 | 0.012 | ✓ | 0.017 | X | 0.839 | ✓ | 58.8 |
| ✓ | A06 | ✓ | 131 | 0.005 | 0.000 | ✓ | 0.005 | ✓ | 0.977 | ✓ | 146.2 |
| ✓ | B31 | ✓ | 221 | 0.000 | 0.005 | ✓ | 0.005 | ✓ | 0.984 | ✓ | 872.6 |
| ✓ | B32 | ✓ | 212 | 0.001 | 0.000 | ✓ | 0.001 | ✓ | 0.985 | ✓ | 409.1 |
| ✓ | B33 | ✓ | 188 | 0.002 | 0.000 | ✓ | 0.002 | ✓ | 0.984 | ✓ | 703.9 |
| ✓ | B34 | ✓ | 193 | 0.000 | 0.000 | ✓ | 0.000 | ✓ | 0.985 | ✓ | 1325.8 |
| ✓ | B35 | ✓ | 208 | 0.000 | 0.000 | ✓ | 0.000 | ✓ | 0.985 | ✓ | 884.0 |
| | PASSING FILTER | | >100 | | | | <0.02 | | >0.95 | | >30 |

FIGURE 6

| PCR Tube A - Sample A | | | PCR Tube B - Sample B | |
|---|---|---|---|---|
| num_reads | EMI Cluster | | num_reads | EMI Cluster |
| 133 | CATTACCGCT | valid EMI clusters | 109 | GAGCTATAGC |
| 122 | AGATCCGATT | | 108 | CTTATCTTTA |
| 120 | GGATCATCGG | | 104 | AGATACCGTT |
| 119 | TTACGCGTAA | | 103 | CAGATGGTAT |
| 112 | TGAGTTATGG | | 102 | GGAGTCCTGG |
| 112 | TAAATAATGT | | 102 | GCCTAAAAGA |
| 111 | GTCCAACTGA | | 93 | TTCGGCAGAA |
| 107 | AGAGTCTTAT | | 92 | GGGGTGGTGT |
| 106 | TACACTCCTT | | 91 | TAATCGTCTA |
| 102 | TGTCATCTTA | | 91 | GTACAGCGCA |
| 102 | GTATTGCGAT | | 73 | TTTGTGTTAT |
| 96 | AATGATTAAT | | 67 | GTTTCAACTT |
| 93 | TATATGGTCA | | 54 | TGTTAAAGAT |
| 81 | GGTGCTATAG | | 48 | GCTCCTTCAT |
| 69 | GTTTAACTGG | | 47 | GTGCGCGGTT |
| 69 | ACGTGATGTA | | 46 | TCTATCTAAG |
| 62 | TTTCATCGGT | | 43 | TCCTGTAAAC |
| 60 | CCTATCCGAT | | 38 | AATAGAATGG |
| 56 | ATAGTAACAT | | 2 | TCATCGTGCG |
| 54 | GGACTATGGT | | 2 | TCACGAGTAC |
| 52 | AATATAGTCA | | 2 | TAGACAAGCG |
| 43 | CTTAGGTGGC | | 2 | CTTGTGTTAT |
| 2 | CTGCCTGGGC | Non-valid EMIs | 2 | CGTGTCTTCT |
| 2 | CTGCCGGCGC | | 2 | CGATGGATGA |
| 2 | ACTTTCCTGC | | 2 | CGAAATTGCG |
| 1 | TTTCTCTTTA | | 1 | TTTTCCAGCT |
| 1 | TTTATGGGCA | | 1 | TGGATATTCG |
| 1 | TTGTAGGTGC | | 1 | TATTATTTAA |
| 1 | TTCGGCAGAA | | 1 | TATCCGACTA |
| 1 | TTCAGAATAC | | 1 | TAGTCTTGTG |

QUALITY CONTROL TEMPLATES ENSURING VALIDITY OF SEQUENCING-BASED ASSAYS

CROSS-REFERENCE TO RELATED APPLICATIONS

This application claims the benefit of U.S. Provisional Application Ser. No. 62/614,236, filed on 5 Jan. 2018, which is incorporated herein in its entirety by this reference.

TECHNICAL FIELD

This disclosure relates generally to the field of genetic sequencing.

BACKGROUND

High throughput sequencing (e.g., next-generation sequencing (NGS)) is increasingly used for diagnostic assays, both whole genome- and exome-sequencing, and more specialized applications such as noninvasive prenatal testing (NIPT), liquid biopsies, and similar assays that detect polymorphisms. In high throughput sequencing (e.g., NGS), cross-contamination is an important concern for clinical applications, because a plurality of samples (e.g., up to 384 samples, etc.) can be processed in the same sequencing run. Particularly, in assays where the mutations or polymorphisms are rare so that their allele frequencies represent only a few percent of the total, cross-contamination from other samples can result in false positives. This is particularly true for NIPT and liquid biopsies, where a quantitative difference of less than a few percent is the difference between a positive and negative outcome.

The standard library preparation practices for high throughput sequencing can require amplification of an initial input DNA sample. These amplification steps can exacerbate the effect of cross-contamination since any amplification of mutant allele in the laboratory can contaminate subsequent samples and experiments, commonly known as PCR carry-over contamination. To prevent this problem, some standard diagnostic assays such as qPCR use dUTP/UNG carry-over prevention systems, in which dUTP is substituted for dTTP in PCR, and uracil-containing amplicons are degraded after the assay through treatment by the enzyme Uracil DNA Glycosylase. However, there is no similar solution for high throughput sequencing-based assays (e.g., NGS-based assays, etc.) despite an even more critical need because of the increased sensitivity of high throughput sequencing (e.g., NGS) and the minute quantitative changes that high throughput sequencing-based assays measure.

While completely eliminating cross-contamination in high throughput sequencing is difficult due to associated chemistry, being able to track it would be similarly valuable. In examples, a different and identifiable sequence can be added to each sample to track its contamination to other wells. However, such examples where each user, each experiment, and each sample has a different library of sequences can be cumbersome and can require the maintenance of a large plurality of distinct libraries (e.g., 384 distinct libraries; a number of distinct libraries corresponding to the number of samples being processed in the same sequencing run; etc.) when used for tracking cross-contamination of multiplexed high throughput sequencing-based assays (e.g., NGS-based assays, etc.). Moreover, such examples would not be able to track PCR carry-over from previous experiments, as the same libraries would be used in different experiments. Furthermore, due to difficulty of maintaining a large plurality of distinct libraries (e.g., 384 distinct libraries, etc.) the identifier sequences themselves can get cross-contaminated. As such, there is a need for new and useful embodiments of a method and/or system, such as for tracking cross-contamination while overcoming these limitations.

BRIEF DESCRIPTION OF FIGURES

FIG. 6 includes a specific example of results associated with quality aspects associated with technician management and/or lab management;

FIG. 10 includes a specific example of determining contamination parameters;

DESCRIPTION OF THE EMBODIMENTS

Figure 1A:
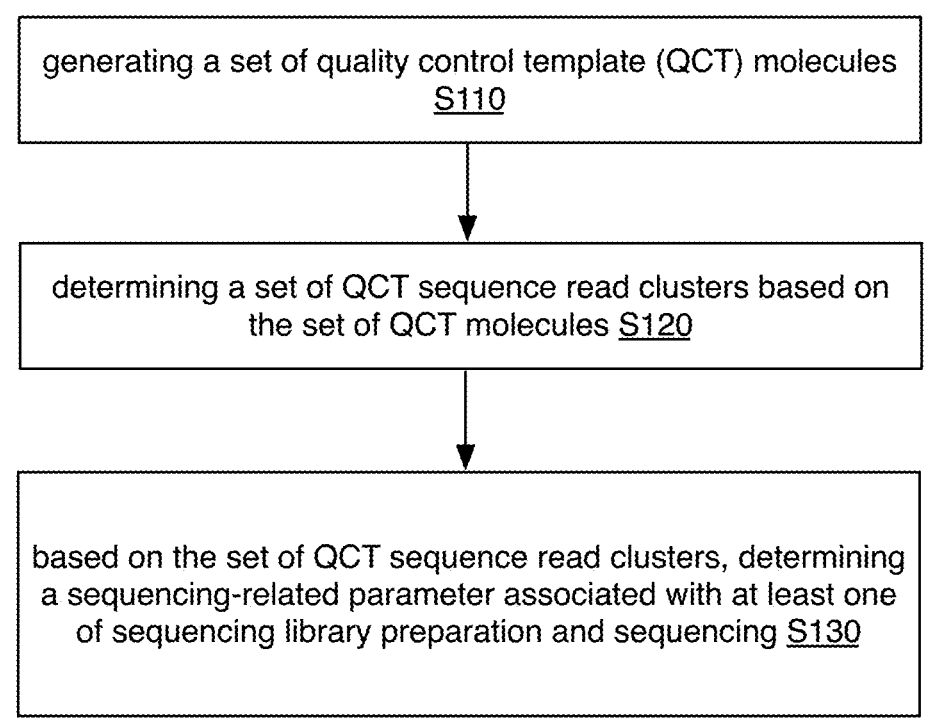
FIGS. 1A-1D include flowchart representations of variations of embodiments of a method.
Figure 1B:
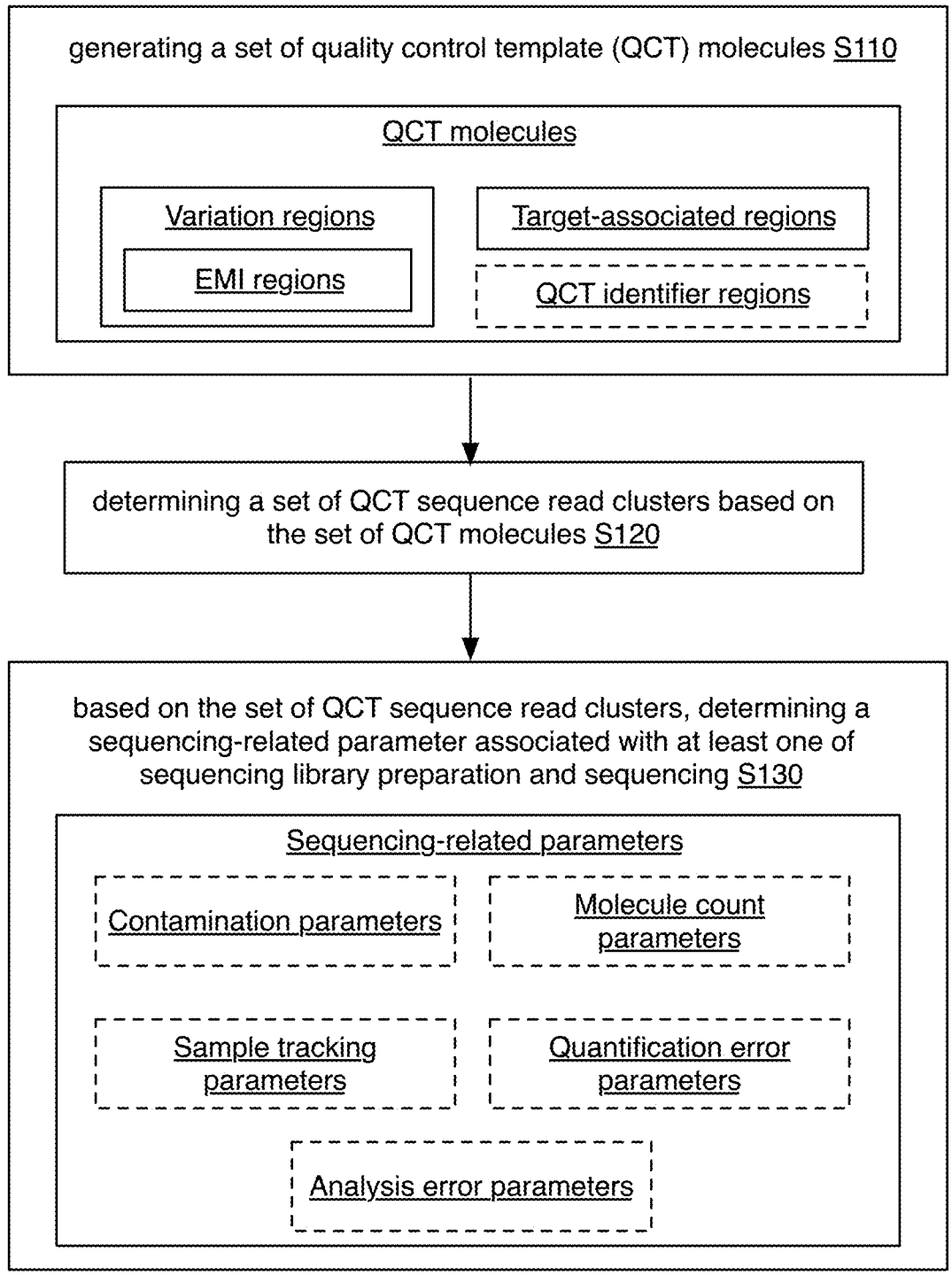
Figure 1C:
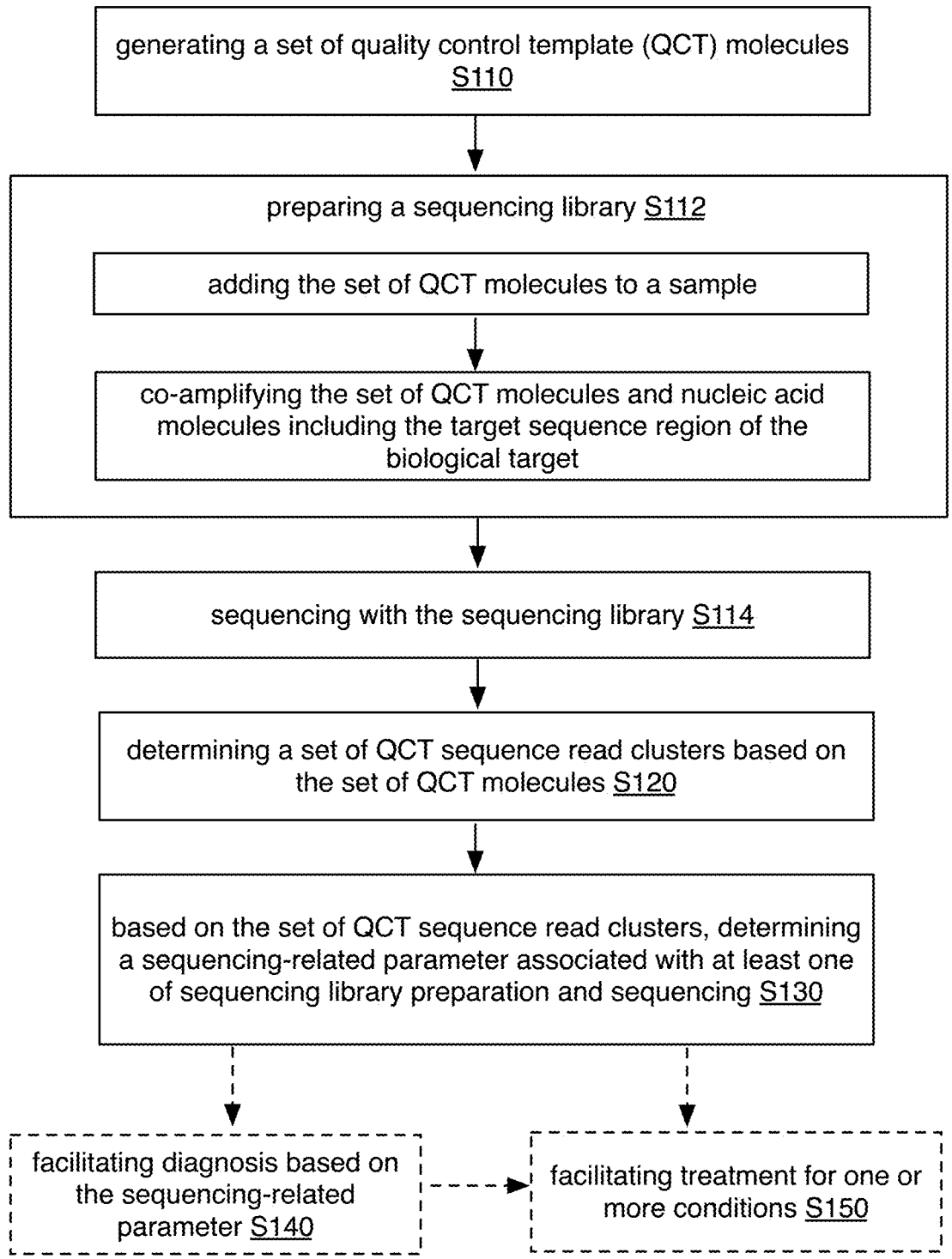
Figure 1D:
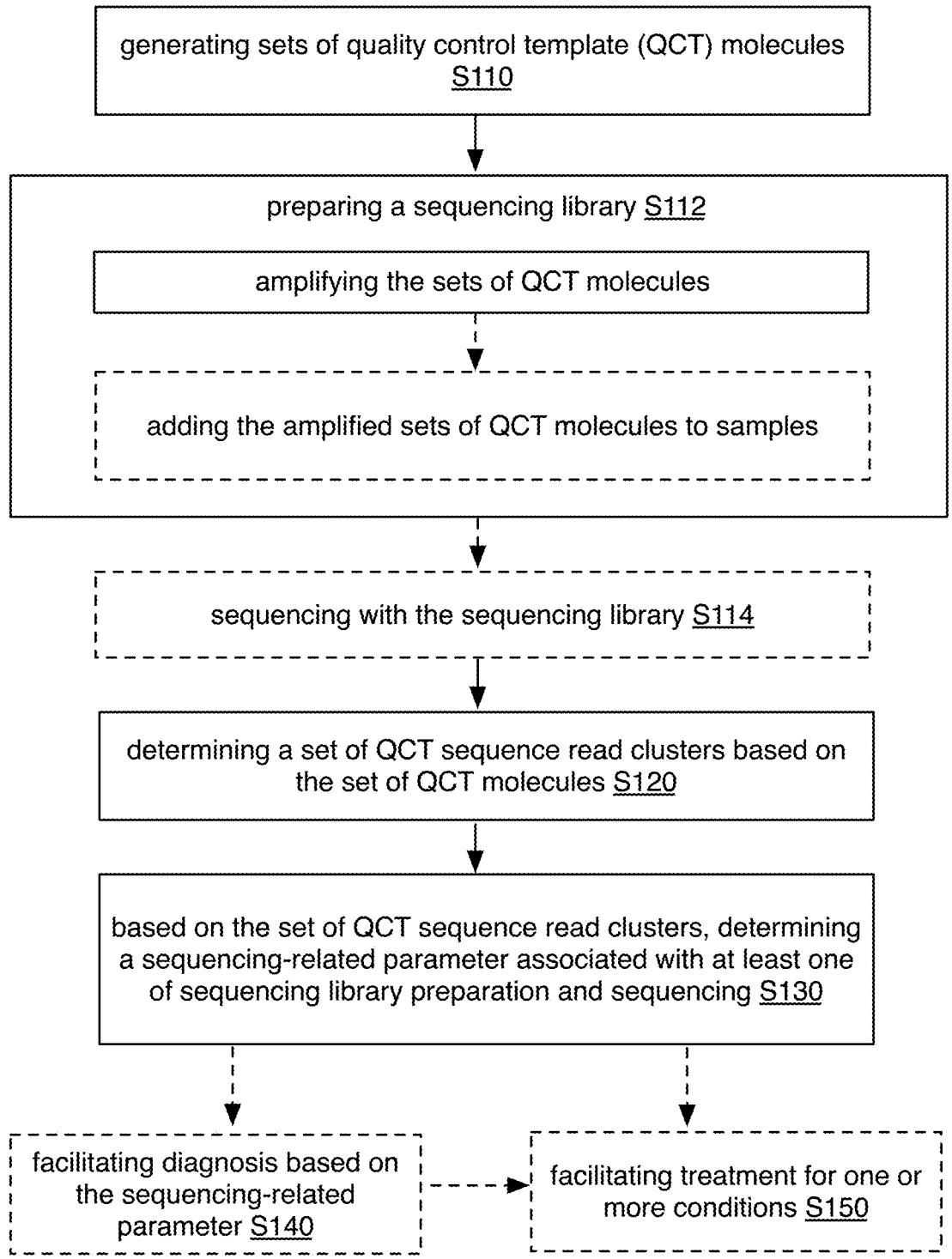

The following description of the embodiments is not intended to be limited to these embodiments, but rather to enable any person skilled in the art to make and use.

1. Overview.

As shown in FIGS. 1A-1D and FIGS. 2-3, embodiments of a method 100 (e.g., for characterization associated with at least one of sequencing library preparation and sequencing; etc.) can include generating a set of quality control template (QCT) molecules (e.g., each QCT molecule including a target-associated region, a variation region, etc.) S110; determining (e.g., computationally; etc.) a set of QCT sequence read clusters (e.g., corresponding to the set of QCT molecules; etc.) based on the set of QCT molecules (e.g., based on the variation regions of the set of QCT molecules; etc.) S120; and/or based on the set of QCT sequence read clusters, determining a sequencing-related parameter (e.g., a contamination parameter, a molecule count parameter, etc.) associated with at least one of sequencing library preparation and sequencing S130.

Additionally or alternatively, embodiments of the method 100 can include preparing one or more sequence libraries S112; sequencing with the one or more sequence libraries S114; facilitating (e.g., aiding, determining, providing, etc.) one or more diagnoses of one or more conditions (e.g., genetic disorders, etc.) S140 (e.g., based on the one or more sequencing-related parameters; etc.); facilitating (e.g., aiding, determining, providing, administering, etc.) treatment for one or more conditions, such as based on sequencing-related parameters, diagnoses, and/or other suitable components S150; and/or any other suitable processes.

In a specific example, the method 100 (e.g., for facilitating prenatal diagnosis of a genetic disorder from a maternal sample associated with a pregnant woman; etc.) can include: adding, to the maternal sample, a set of QCT molecules associated with the genetic disorder, the set of QCT molecules including: target-associated regions with sequence similarity to a target sequence region of endogenous target molecules (e.g., associated with the genetic disorder; etc.), and variation regions (e.g., including embedded molecular identifier (EMI) regions including a set of variable "N" bases, where each "N" base is selected from any one of an "A" base, a "G" base, a "T" base, and a "C" base, etc.) with sequence dissimilarity to a sequence region of the endogenous target molecules; generating a co-amplified mixture based on co-amplifying the set of QCT molecules and nucleic acid molecules (e.g., nucleic acids; nucleic acid fragments; etc.) including the target sequence region; sequencing the co-amplified mixture; computationally determining a unique number of the set of QCT molecules, based on a number of the variation regions that are distinct and detected from QCT molecule sequence reads from the sequencing, where the QCT molecule sequence reads correspond to the set of QCT molecules; calculating the average QCT sequencing depth based on dividing a number of the QCT molecule sequence reads by the unique number of QCT molecules; determining an absolute count of the endogenous target molecules based on dividing a total read count for the endogenous target molecules by the average QCT sequencing depth; determining an absolute count of endogenous reference molecules based on dividing a total read count for the endogenous reference molecules by the average QCT sequencing depth; and facilitating the prenatal diagnosis of the genetic disorder based on a comparison between the absolute count of endogenous target sequences and the absolute count of endogenous reference sequences.

In a specific example, the method 100 (e.g., for characterization, such as identifying contamination, associated with at least one of sequencing library preparation and sequencing; etc.) can include generating a set of QCT molecules, each QCT molecule including a variation region (e.g., including one or more EMI regions, etc.) and/or a target-associated region (e.g., with sequence similarity to a target sequence region of a biological target, etc.); computationally determining a set of QCT sequence read clusters based on the variation regions of the set of QCT molecules, such as where the set of QCT sequence read clusters includes QCT molecule sequence reads derived from the sequencing corresponding to a QCT mixture generated based on the set of QCT molecules and a sample including the biological target (e.g., a sample including endogenous target molecules corresponding to the biological target; etc.), such as where the sequencing library preparation includes co-amplification, of the set of QCT molecules and nucleic acid molecules including the biological target (e.g., based on the sequence similarity of the target-associated region and the target sequence region of the biological target, etc.); and based on the set of QCT sequence read clusters, determining a sequencing-related parameter associated with at least one of the sequencing library preparation and the sequencing (e.g., determining a contamination parameter describing the contamination associated with at least one of the sequencing library preparation and the high throughput sequencing, etc.).

Figure 2:
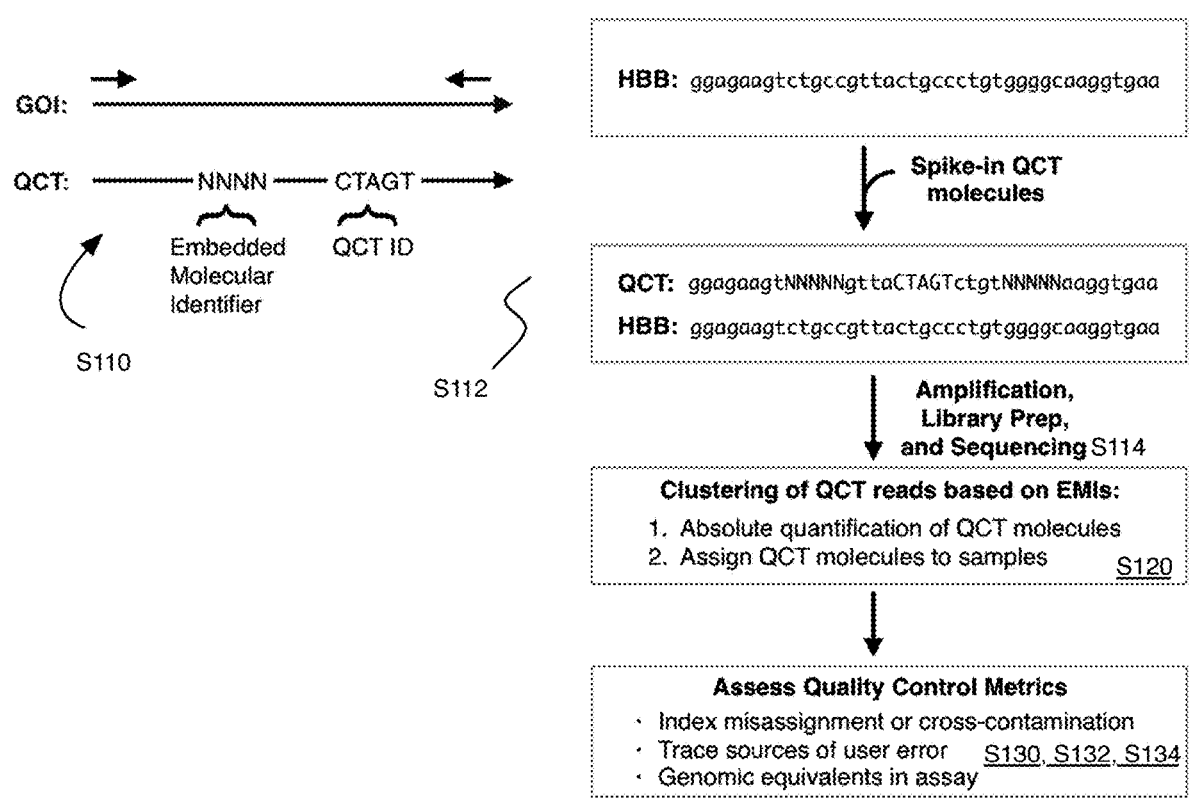
FIG. 2 includes a flowchart representation of a variation of an embodiment of a method.
Figure 3:
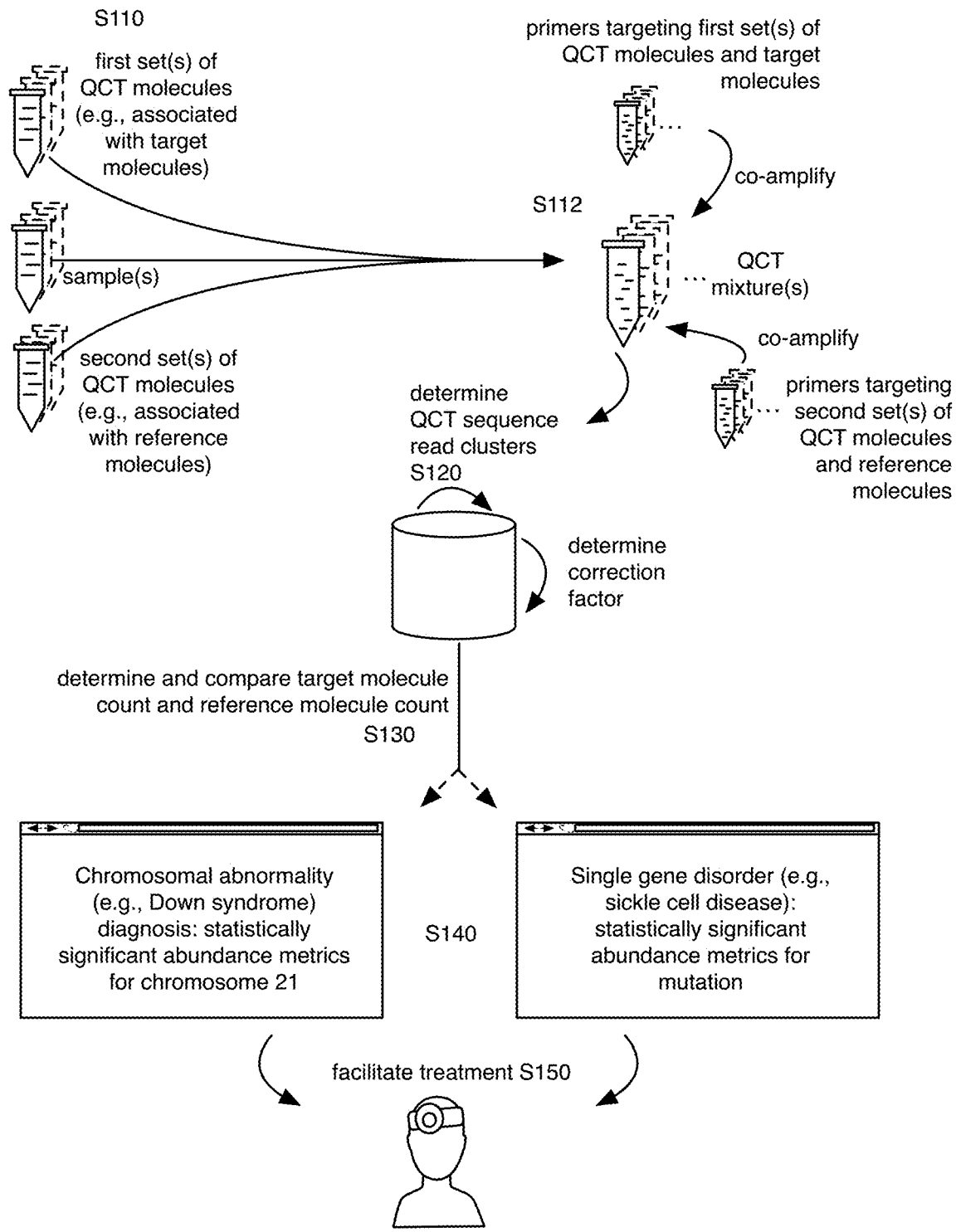
FIG. 3 includes a flowchart representation of a variation of an embodiment of a method.

In a specific example, as shown in FIG. 2, the method 100 (e.g., for ensuring validity of sequencing-based assays based on QCT molecules; etc.) can include: generating a QCT library or mixtures of QCT libraries of QCT molecules (e.g., QCT DNA including target-associated regions with high similarity to a gene of interest to enable co-amplification using the PCR primers depicted as black arrows in FIG. 2; QCT DNA including variation regions with sequence differences compared to the gene of interest, such as where the variation region can include an EMI region including "N" bases that can randomly adopt "A", "C", "T", or "G" bases, such as where up to 4^4 unique EMI sequences can be generated with "NNNN", such as where the probability of two QCT molecules having the same EMI can be found using the solution to the birthday problem for computing hash collision probability, such as where subsections of QCT and HBB sequence differences can be shown in FIG. 2; QCT DNA including a QCT identifier (QCT ID) region for distinguishing QCT libraries and gene of interest sequences in sequencing reads; etc.); preparing a sequencing library based on the QCT molecules and one or more samples including the biological targets (e.g., HBB, as shown in FIG. 2; etc.), such as by spiking-in the QCT library to the human DNA; applying computational approaches to cluster QCT molecule sequence reads (e.g., based on EMI sequence similarity; where the number of EMI clusters corresponds to the absolute number of QCT molecules spiked-in to the sample; etc.) and assign the clusters to different sample identifiers (e.g., corresponding to different samples; corresponding to different sample compartments used in the sequencing; etc.); and using such data to assess quality control metrics such as cross-contamination, index misassignment, user errors (e.g., in executing the assay), non-compliance with assay parameters (e.g., too small of an amount of input DNA, accessible genomic equivalents in a sample; etc.), and/or to quantify the amount of input biological target that is accessible by an assay.

Embodiments of the method 100 and/or system 200 can function to accurately quantify the abundance of biological targets, accurately track and/or quantify the degree of contamination (e.g., cross-contamination across different samples, different experiments; true contamination levels associated with use of unique dual index primers; etc.), identify user errors in executing sequencing-based assays, monitor sequencing index misassignment, determine non-compliance with assay parameters, identify and/or facilitate removal of contaminating and/or index-hopping primers, and/or improve any suitable aspects associated with sequencing library preparation and/or sequencing, such as for improving diagnostics and/or therapeutics.

In an example, a single reagent (e.g., including a set of a QCT molecules, etc.), can be added to a set of samples to track cross-contamination as well as other user errors by adding a single reagent to all the samples is disclosed herein. In an example, the addition of QCT molecules, when accompanied by a custom mathematical and computational analysis pipeline based on solutions to the birthday problem for hash collision, can track cross-contamination across different users, different experiments, and different samples at the same time. In examples, a single QCT library can be added to all samples (e.g., associated with the high-throughput sequencing; etc.), such as for improving the user-friendliness and convenience. In a specific example, distinct QCT libraries (e.g., corresponding to different QCT identifier regions such as QCT IDs, etc.) can be added at different stages of sample preparation to track any user error or loss of input sample. In examples, an automatic fingerprint-on-dispense approach can be applied, where each sample can be identified by the QCT molecules (e.g., based on variation regions of the QCT molecules; QCT identifier regions of the QCT molecules; etc.). In examples, contamination due to PCR carry-over can be measured, which such contamination can be a concern in clinical environments and/or other contexts. In specific examples, QCT molecules can be used to assign a molecular fingerprint to every PCR tube, and PCR carry-over can be detected and quantified by maintaining a database of all variation regions (e.g., EMI sequences of EMI regions, etc.) associated with every PCR tube performed at a given laboratory location or room. Carry-over PCR in subsequent assays can then be identified by computationally searching for variation region fingerprint (e.g., EMI fingerprint similarities, etc.) in the historical database.

Figure 4A:
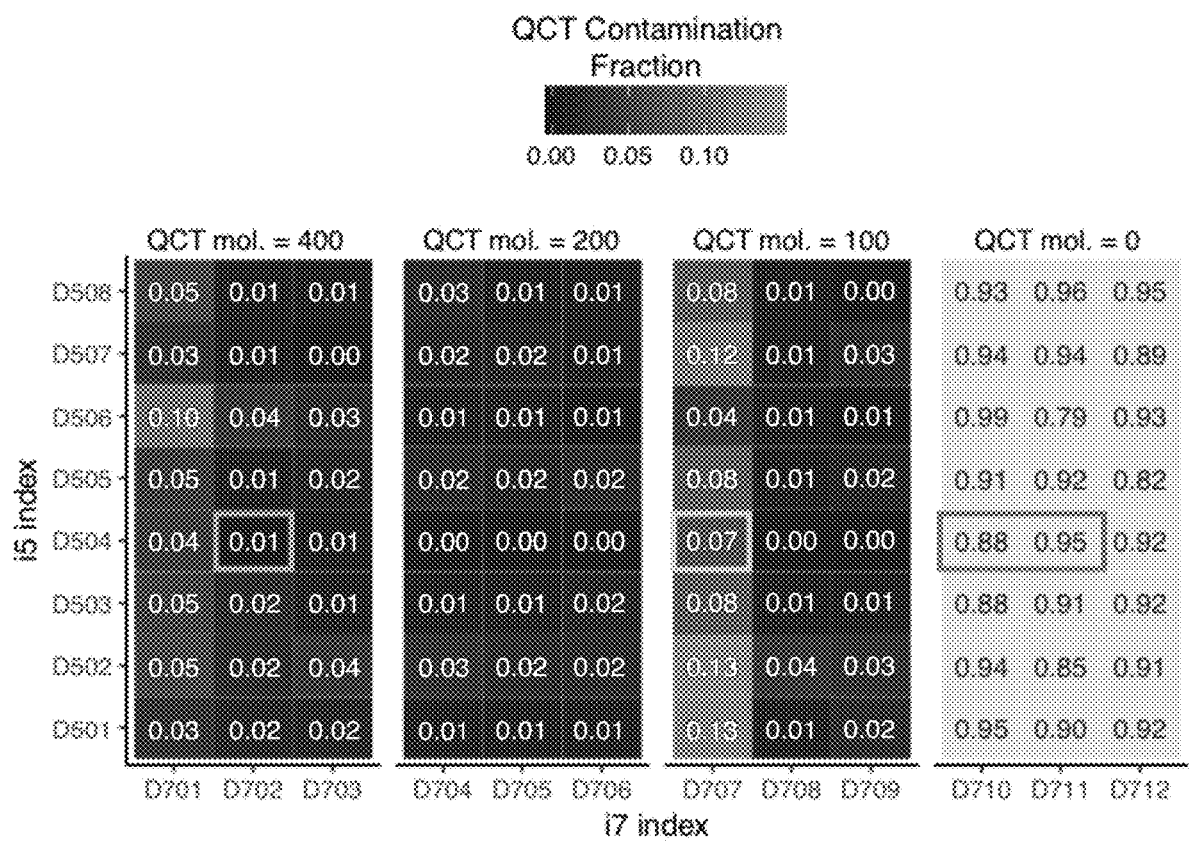
FIGS. 4A-4D include graphical representations of results from validating portions of a variation of an embodiment of a method, in particular in relation to cross-contamination and index misassignment.
Figure 4B:
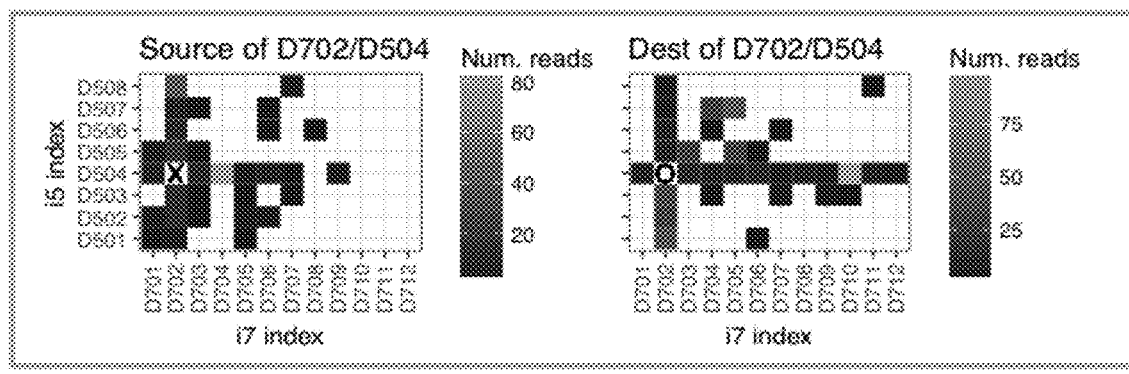
Figure 4C:
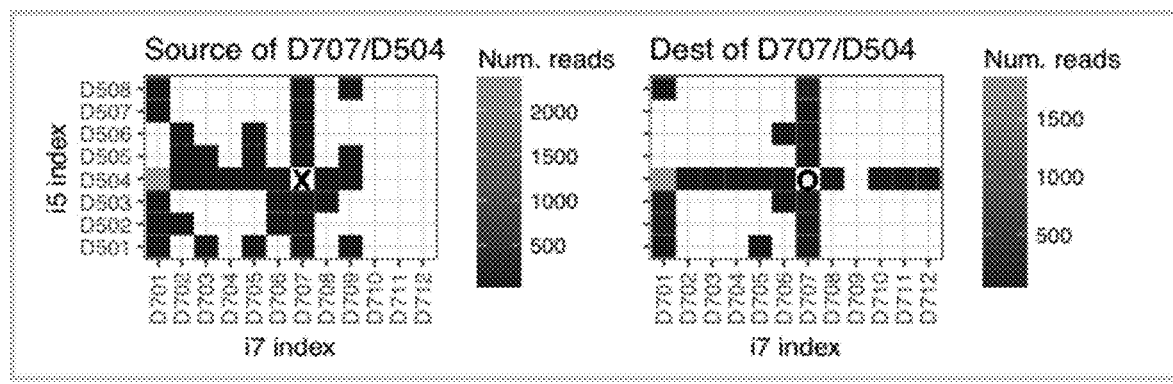
Figure 4D:
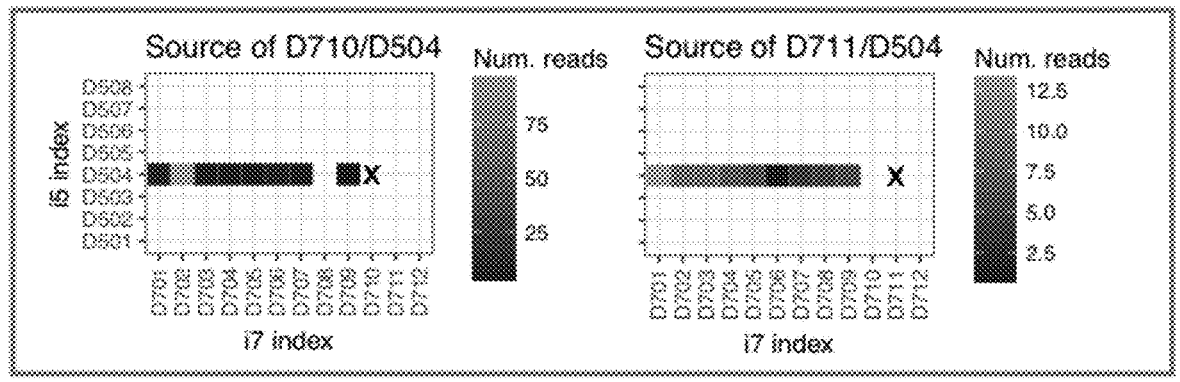

Embodiments can additionally or alternatively be used for quality assurance against an important concern for high throughput sequencing (e.g., NGS, etc.) namely, "index switching" or index misassignment. In examples, even in the absence of any cross-contamination, sequencing reads or signals (e.g., up to 5-10%; etc.) from one sample can be misassigned to another sample when multiplexed on the same flow cell. In examples, a convenient fingerprint-on-dispense approach can be performed to accurately quantify the degree of misassignment in every sample. In a specific example, as shown in FIGS. 4A-4D, the cumulative effect of cross-contamination in nearby wells and index misassignment can be detected at >90% sensitivity. In a specific example, as shown in FIG. 4A, an Illumina Truseq HT library can be prepared using all 96 combinations of i7 and i5 indices, where each well corresponds to an HBB amplicon sequencing experiment with 400, 200, 100, or 0 QCT molecules added to each well; shown in each well is the fraction of QCT reads identified as cross-contamination, where in the experiment, cross-contamination and index misassignment ranged between <1% to up to 13%; due to o QCT molecules in D710-D712 columns, the fraction in these wells indicates the sensitivity with which the variations of embodiments of the method 100 can detect cross-contamination; and where FIG. 4B illustrates number and source of contaminating reads found in D702/D504, indicated by X (left); and number and destination of contaminating reads that originate from D702/D504, indicated by O (right); and where FIG. 4C illustrates an analogous analysis as for FIG. 4B, but for the well D707/D504; and where FIG. 4D illustrates the source of contamination for wells D710/D504 and D711/D504, and where no contaminating reads were found to be originating from these wells, consistent with the absence of QCT molecules added to these wells.

Figure 5A:
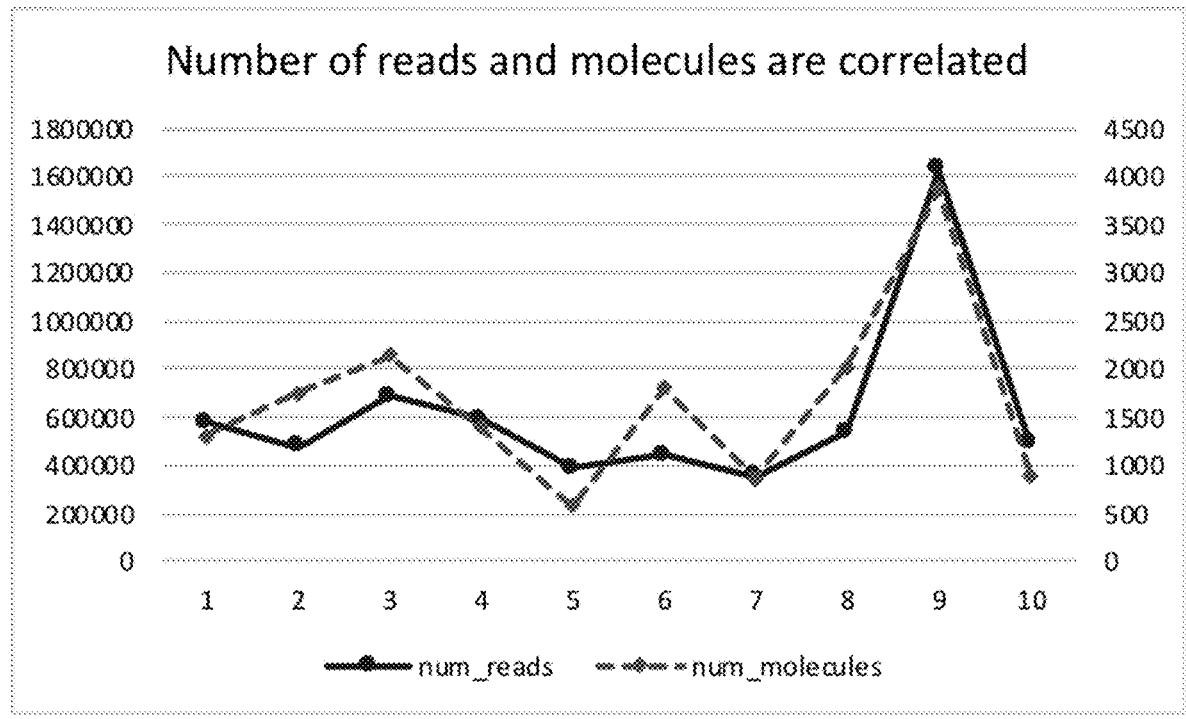
FIGS. 5A-5B include a specific example of results from experiments validating the use of QCT molecules for molecular counting.
Figure 5B:
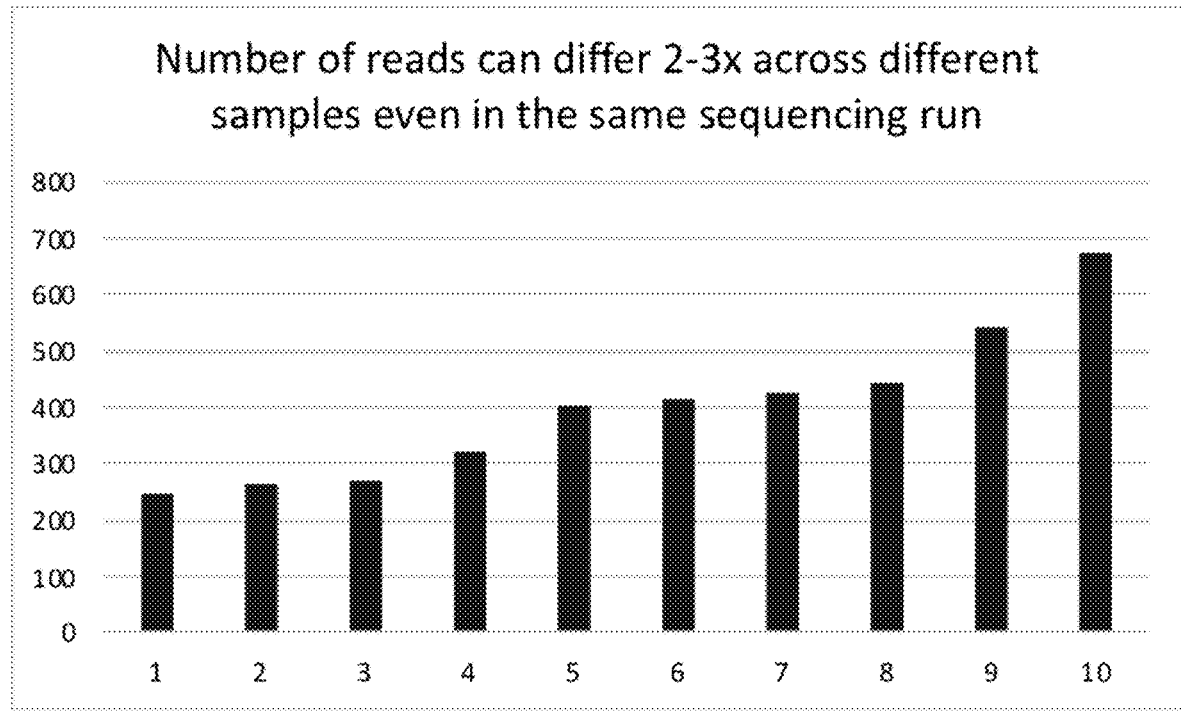
Figure 7A:
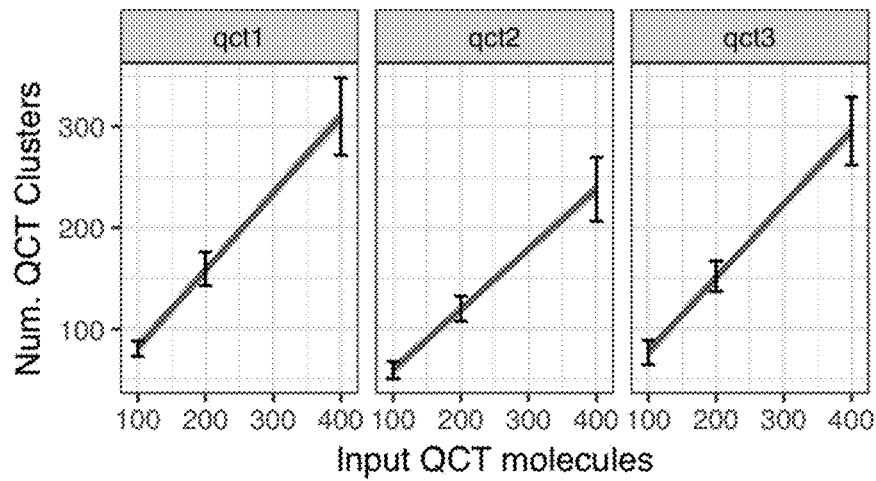
FIGS. 7A-7C include graphical representations of results from validating portions of a variation of an embodiment of a method, in particular in relation to quantification of QCT molecules.
Figure 7B:
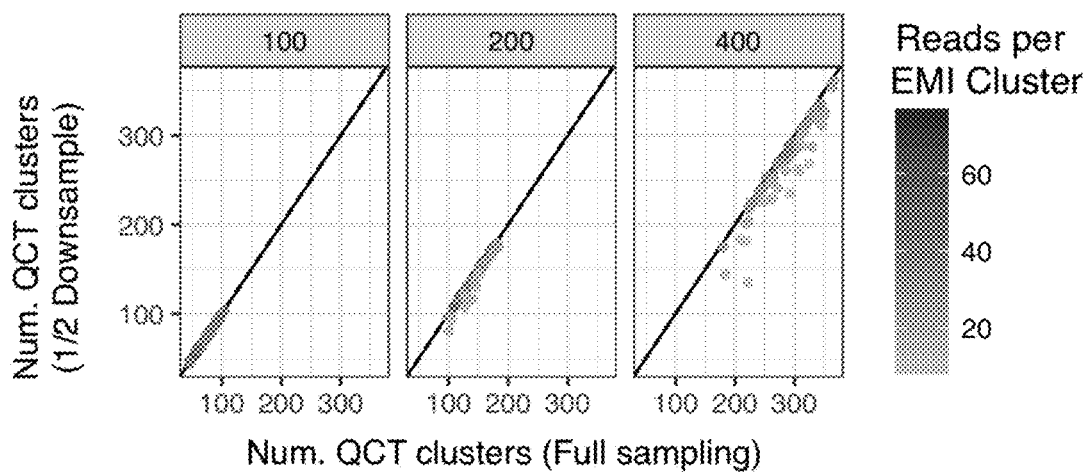
Figure 7C:
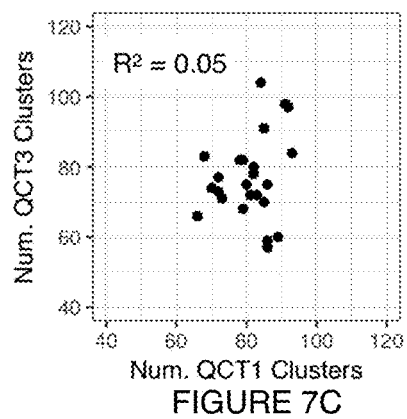

Embodiments can additionally or alternatively enable accurate molecular counting of a biological target (e.g., based on the use of a set of variation regions of a set of QCT molecules, etc.), such as when read depth is sufficient (e.g., greater than twenty read depth per distinct QCT molecule; etc.), which can aid in obtaining accurate target quantification in approaches that use the addition of complex sequences. Embodiments can quantify the accessible biological target that is assayed when read depth is sufficiently high. In an example, pertaining to the detection of mutations for use in noninvasive prenatal testing by amplicon sequencing, such high read depth for a complex sequence is obtained when <400 QCT molecules are added to each sample, such as where 96 such samples are multiplexed on a MiSeq run (e.g., as shown in FIG. 7C). However, any suitable number of QCT molecules can be added to one or more samples for facilitating molecular counting and/or other suitable functionality. In specific examples, as shown in FIGS. 5A-5B, the number of sequence reads and number of molecules (e.g., determined based on the sequence reads and the processing associated with the QCT molecules; etc.) can be correlated, and where the ratio between the number of molecules and reads can differ by 2-3×, indicating the improvements associated with using QCT molecules to determine the number of molecules in a given sample (e.g., improvements in reliability over using the number of reads by itself; etc.).

In examples (e.g., of quantifying absolute molecule count for one or more biological targets, etc.), the method 100 and/or system 200 can be used a) to determine parameters for use in algorithms for determining the diagnostic outcome of assays, b) to track the loss of input DNA at different stages of experiments or assays, c) to return a no-call result when the number of target molecules is too low (e.g., to determine when an assay is not reliable, etc.), d) to design assays for detecting copy number variation at a particular locus or across loci, and/or e) aiding therapeutic and clinical decision-making based on the results of diagnostic assays.

Embodiments can additionally or alternatively assess and/or improve several quality aspects associated with technician management and/or lab management (e.g., clinical lab management; etc.). As shown in FIG. 6, in a specific example, the method 100 and/or system 200 can be used to identify problematic sample processing by different technicians or laboratories, where Samples A01 through A06 vs. Samples B31 through B35 were run in two different laboratories with different pre/post-PCR separation practices; the same volume of QCT molecules from the same kit, which roughly corresponded to ~200 molecules, was added to each sample before processing; "num_seqs" indicate number of distinct EMI clusters that were identified for each sample; "contam_frac" indicates the total fraction of contaminating reads that were identified in each sample; "collision_frac" identifies the degree to which two valid EMI clusters are found in two different sample; "contam_collision_frac" combines the previous two metrics; "ident_frac" is the number reads that map to valid EMIs divided by total number of reads for that particular sample; "reads_per_qct-mol" indicates the average read-depth for EMIs; a filter threshold was used for these derived metrics to identify samples that pass or do not pass quality-control (QC); where only 1 out of 6 samples passed QC metrics for Laboratory A whereas 5 out of 5 samples passed QC metrics in Laboratory B; and where these results can be used to change how sample processing and pre/post-PCR separation can be conducted (e.g., where in Laboratory A, in the next run with improvements in the sample processing, samples passed the same QC metrics; etc.). As shown in FIGS. 7A-7C, in specific examples, by including multiple species of QCTs that are dispensed from the same pool, random error in pipettes via the correlation of absolute counts of QCT molecules can be measured (e.g., as shown in FIG. 7C), and/or systematic pipette and/or quantification error can additionally or alternatively be traceable (e.g., as shown in FIG. 7A, such as based on a comparison of the middle panel versus the left and right panels). In specific examples, as shown in FIGS. 7A-7C, absolute quantification of spiked-in QCT molecules can be determined. In a specific example, as shown in FIG. 7A, QCT1, QCT2, and QCT3 libraries (e.g., corresponding to different sets of QCT molecules; etc.) can be prepared, pooled, and spiked-in to PCR reactions at 100, 200, or 400 molecules per QCT library; EMIs for each QCT library can be clustered by aggregating EMI sequence reads with at most 2 base changes; error bars can represent mean +/− standard deviation for 24 replicates; and graph lines can represent a linear regression fit with shading corresponding to 95% confidence interval of mean. In a specific example, as shown in FIG. 7B, to determine the robustness of QCT counting to read depth, sequencing reads can be downsampled by randomly selecting ½ of the total reads; the number of EMI clusters recovered from down-sampled sequencing reads can be plotted against the full dataset; the color of the points can represent the down-sampled read depth per EMI cluster, where the black line has slope=1, intercept=0; QCT analysis is robust when read depth per QCT molecule is more than 20, which can aid reliability of molecular counting; and when number of QCT clusters is 400, down sampled read depth is less than 20 per molecule. In a specific example, as shown in FIG. 7C, QCT molecule counts can be uncorrelated across QCT libraries (e.g., as expected, etc.); where a scatter plot of numbers of QCT3 clusters vs. QCT1 clusters can be shown for each PCR replicate from FIG. 7A at the 100 QCT molecule input level.

Embodiments can additionally or alternatively deploy QCT libraries at different sequencing library preparation stages (e.g., sample preparation stages) and/or sequencing stages to trace loss-of-sample. In a specific example, if a first set of QCT molecules (e.g., QCT1 molecules; first QCT molecules including a first shared QCT identifier region; etc.) is dispensed at the point of sample collection, and an equal amount of a second set of QCT molecules (e.g., QCT2 molecules; second QCT molecules including a second shared QCT identifier region; etc.) is dispensed after sample purification, the purification yield may be assessed via comparisons of molecules counts for the first set of QCT molecules and the second set of QCT molecules (e.g., QCT1 vs QCT2 molecule counts, etc.).

Figure 8A:
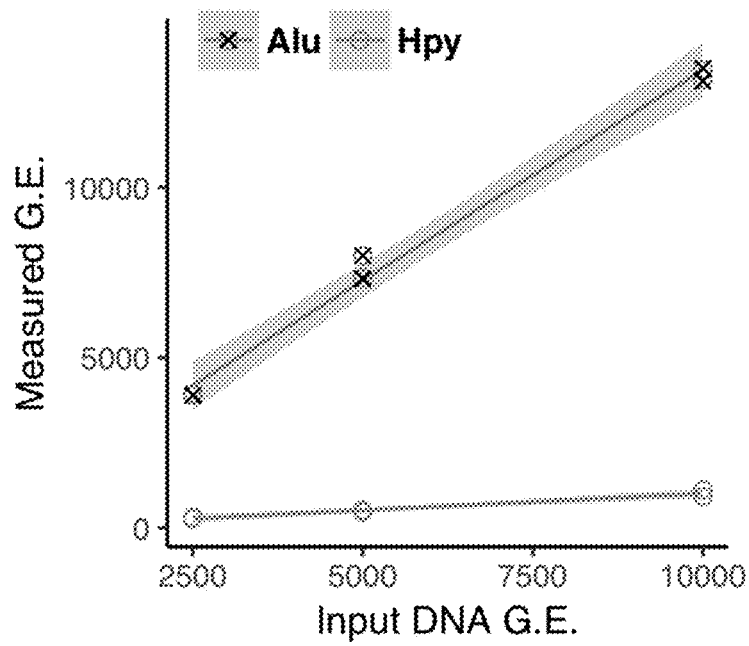
FIGS. 8A-8B includes graphical representations of results from validating portions of a variation of an embodiment of a method, in particular in relation to quantification of biological targets.
Figure 8B:
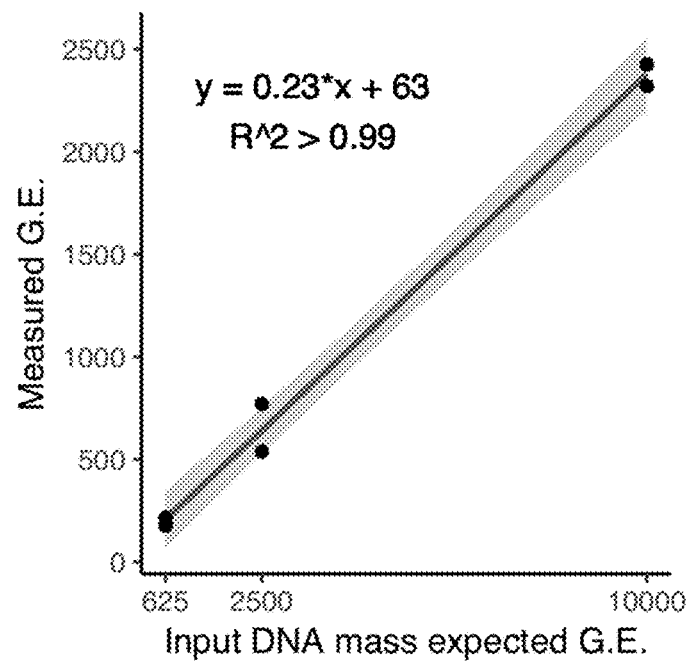
Figure 9:
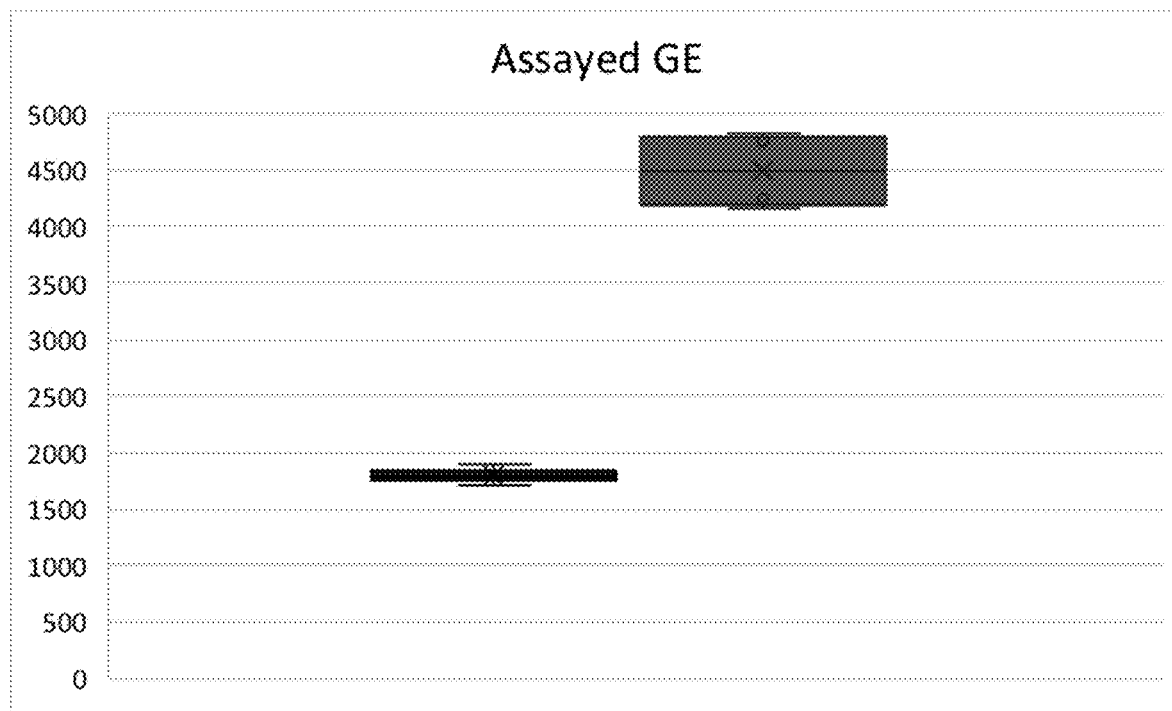
FIG. 9 includes a specific example of using QCT molecules to measure assayable genomic equivalents.

Embodiments can additionally or alternatively determine the portion of biological material that is accessible by the assay, such as through quantification of the biological targets based on using the QCT molecules, which can improve upon measuring the total genomic material available and calculating the expected biological target concentration, due to not all targets being accessible by assays. In a specific example, this may be due to shearing of DNA to a short size distribution, as in the case of circulating free DNA that is assayed in applications of noninvasive prenatal testing (NIPT) for determination of genetic conditions in the fetus and liquid biopsy applications where circulating tumor DNA is assayed. In a specific example, in these applications, depending on the target of interest, less than 25% of the DNA may be accessible, where, as shown in FIGS. 8A-8B, determination of input DNA genomic equivalents can be determined using QCT molecules, such as where human genomic DNA can be restriction enzyme digested by either Alu or Hpy, which cut outside and inside of the gene of interest, respectively; QCT molecules can then be spiked-in to 9 ng-36 ng of digested DNA (corresponding to 2,500-10, 000 genomic equivalents), amplified by PCR, and sequenced on a MiSeq; the genomic equivalents (G.E.) of human DNA in each PCR reaction can be measured by analyses associated with the QCT molecules in applying portions of embodiments of the method 100; PCR reactions can be performed in duplicate, where FIG. 8A illustrates a linear fit line and shading is 95% CI of mean, and where the measurement of input DNA is consistent across replicates and through dilution series but is systematically higher than the Qubit measurement by a constant factor; and where, as shown in FIG. 8B, human genomic DNA can be sheared to a size distribution with a peak at 100-150 bp; QCT molecules can then be spiked in to 2.3 ng-36 ng of sheared DNA, and the genomic equivalents of sheared DNA can be measured, with an amplicon size of ~150 bp, and where FIG. 8B illustrates the slope of the line indicating the fraction of molecules that can be amplified due to random shearing. In a specific example, as shown in FIG. 9, QCT molecules can be used to measure assayable genomic equivalents, which can be different for each assay, and even for the same assay with different footprints; where the region surrounding the same mutation was amplified from sheared DNA to form a 150-bp PCR product vs. 72-bp PCR product (left vs. right), and QCT molecules were used to measure the number of molecules amplified in both cases; where 18 nanograms (ng) of genomic DNA corresponding to 5000 input genomic equivalents was sheared to an average length of ~170 bp (e.g., the average length of circulating free DNA) and was included in all cases (n=8 for 150-bp and n=4 for 72-bp); and consistent with theoretical models, the number of molecules that can be amplified is significantly less than the input DNA and can have as much as 2× difference among different footprints for the same input DNA mass; and where FIG. 9 can indicate why other measurements of input DNA (such as concentration) may not be sufficient for precise molecular diagnostics that require molecular information, such as where ~2× decrease in the molecular count would increase its Poisson noise by ~40%, which can be the difference between 95% (2 sigma) and 99% (3 sigma) accuracy.

Embodiments of the method 100 and/or system 200 can be used in association with one or more conditions (e.g., in association with characterizing, diagnosing, treating, and/or performing processes related to one or more conditions; etc.), where the conditions can include and/or otherwise be associated with one or more of: noninvasive prenatal testing (NIPT) (e.g., in relation to genetic screening for presence of chromosomal abnormalities including aneuploidy, such as trisomy 21 or Down syndrome, trisomy 18 or Edwards syndrome, trisomy 13 or Patau syndrome, sex chromosome aneuploidies such as Turner syndrome, other suitable aneuploidies; chromosomal abnormalities including DiGeorge syndrome; in relation to genetic screening for single gene disorders; etc.); other prenatal testing; aneuploidy analysis and/or other suitable analysis outside of a prenatal context; genetic disorders (e.g., single gene disorders including sickle cell disease; chromosomal abnormalities; disorders associated with gene amplification; gene deletion; partial chromosomal abnormalities; 22q11.2 deletion syndrome or DiGeorge syndrome; Charcot-Marie-Tooth syndrome, cystic fibrosis, Huntington's disease; Duchenne muscular dystrophy; hemophilia, thalassemia; etc.), other applications associated with chromosome abnormalities (e.g., additional, missing, irregular chromosomal DNA, etc.), cancer (e.g., through analyses associated with any suitable oncogenes, cancer biomarkers, and/or other cancer-associated targets; through analyses associated with liquid biopsies), and/or any other suitable conditions. In an example, the method 100 can include determining a target molecule count (e.g., corresponding to a number of target molecules in a sample; based on use of QCT molecules; etc.) for facilitating diagnosis associated with at least one of noninvasive prenatal testing and liquid biopsies. Conditions additionally or alternatively include: psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); cardiovascular-related conditions (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; chronic disease; and/or any other suitable type of conditions.

Sequencing (e.g., in relation to S112) associated with one or more embodiments of the method 100 and/or system 200 preferably includes high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. Additionally or alternatively, sequencing can include any suitable sequencing technologies (e.g., Sanger sequencing, capillary sequencing, etc.).

One or more instances and/or portions of embodiments of the method 100 and/or processes described herein can be performed asynchronously (e.g., sequentially), concurrently (e.g., in parallel; concurrently processing biological samples in a multiplex, automated manner; concurrently computationally processing sequence reads to improve system processing ability; etc.), in temporal relation to a trigger event, and/or in any other suitable order at any suitable time and frequency by and/or using one or more instances of embodiments of the system 200, components, and/or entities described herein.

Additionally or alternatively, data described herein (e.g., clusters, sequencing-related parameters, identifiers, read depths, sequence reads, sequence region determinations, QCT molecule designs, primer designs, etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data, such as temporal indicators indicating the sequence of stages of sequencing library preparation and/or sequencing; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data described herein can be associated with value types including any one or more of: scores, binary values, classifications, confidence levels, identifiers (e.g., sample identifiers, QCT molecule identifiers, etc.), values along a spectrum, and/or any other suitable types of values. Any suitable types of data described herein can be used as inputs, generated as outputs, and/or manipulated in any suitable manner for any suitable components associated with embodiments of the method 100 and/or system 200.

Embodiments of the system 200 can additionally or alternatively include a sample handling network configured to generate molecules (e.g., QCT molecules; QCT libraries; etc.), process biological samples, and/or perform other suitable processes; a sequencing system configured to sequence processed genetic material from mixtures generated based on biological samples and QCT molecules; a computing system (e.g., a remote computing system; a local computing system; etc.) configured to analyze the sequence reads, determine QCT sequence read clusters, determine sequencing-related parameters, facilitate diagnoses, facilitate treatment, and/or perform other suitable processes (e.g., computational processes); and/or any other suitable components. The components of the system 200 can be physically and/or logically integrated in any manner (e.g., with any suitable distributions of functionality across the components, such as in relation to portions of embodiments of the method 100; etc.). However, the method 100 and system 200 can be configured in any suitable manner.

2.1 Generating QCT Molecules.

Embodiments of the method 100 can include generating a set of QCT molecules S110, which can function to generate molecules to be used (e.g., added, processed, sequenced, etc.) at one or more stages (e.g., steps, phases, periods, time periods, etc.) of at least one of sequencing library preparation and sequencing (e.g., high-throughput sequencing, etc.), such as for facilitating downstream computational processing (e.g., QCT sequence read cluster determination for facilitating sequence-related parameter determination; etc.).

QCT molecules preferably include target-associated regions (e.g., one or more target-associated regions per QCT molecule; etc.). As shown in FIG. 2, target-associated regions preferably include sequence similarity (e.g., full sequence similarity; sequence similarity satisfying a threshold condition; sequence similarity of a specified number of bases; etc.) to one or more target sequence regions of one or more target molecules (e.g., endogenous target molecules; corresponding to one or more biological targets; etc.), but can additionally or alternatively include any suitable association with any suitable components of one or more target molecules. Target-associated regions preferably enable co-amplification of the corresponding QCT molecules (e.g., including the target-associated regions, etc.) and nucleic acid molecules (e.g., nucleic acids, nucleic acid fragments, etc.) including the target sequence region, which can facilitate improved accuracy in molecular counting (e.g., in determining molecule count parameters; by accounting for amplification biases; etc.), but can additionally or alternatively enable any suitable processes associated with the sequencing library preparation, sequencing, and/or portions of embodiments of the method 100. In an example, sequencing library preparation (e.g., performing sequencing library preparation S112) can include co-amplification, of the set of QCT molecules and nucleic acid molecules including the biological target, based on the sequence similarity of the target-associated region and the target sequence region of the biological target, and where determining the sequencing-related parameter can include determining a target molecule count describing a number of molecules of the biological target associated with the sequencing, based on the set of QCT sequence read clusters.

In variations, QCT molecules can omit target-associated regions. For example, QCT molecules can be used with components of samples including biological targets, without target-association (e.g., without having pre-determined similarity to target sequence regions of the biological targets) and/or without corresponding co-amplification with components of the samples (e.g., nucleic acid molecules including the target sequence regions; etc.). In examples, QCT molecules can be pre-processed to be adapted to sequencing, such as where the pre-processed QCT molecules can be added to a processed sample suitable for sequencing, to be co-sequenced without the need for co-amplification (e.g., for improving user friendliness). QCT molecules omitting target-associated regions are preferably usable for facilitating contamination parameter determination but can additionally or alternatively be used for facilitating any suitable sequencing-related parameter determination. In a specific example, the set of QCT molecules can be adapted for subsequent sequencing (e.g., high-throughput sequencing such as NGS; etc.), where generating the set of QCT molecules can include amplifying a first subset of QCT molecules (e.g., each including a first shared QCT identifier region; etc.) of the set of QCT molecules; and amplifying a second subset of QCT molecules (e.g., each including a second shared QCT identifier region; etc.) of the set of QCT molecules, where the QCT molecule sequencing reads are derived from the sequencing corresponding to: a QCT mixture generated based on the first subset of QCT molecules and the sample including the biological target (e.g., including first target molecules corresponding to the biological target; etc.), and an additional QCT mixture generated based on the second subset of QCT molecules and an additional sample including the biological target (e.g., including second target molecules corresponding to the biological target; etc.), where the sample and the additional sample respectively correspond to a first sample compartment and a second sample compartment of the sample compartments. However, target-associated regions and/or QCT molecules omitting target-associated regions can be configured in any suitable manner.

QCT molecules preferably include one or more variation regions (e.g., one or more variation regions per QCT molecule; adjacent variation regions; separated variation regions; etc.). As shown in FIG. 2, a variation region preferably includes sequence dissimilarity (e.g., complete sequence dissimilarity; dissimilarity of a specified number of bases; partial sequence dissimilarity; etc.) to one or more sequence regions (e.g., distinct from a target sequence region; etc.) of target molecules. A variation region can additionally or alternatively include one or more EMI regions. In a variation, an EMI region can include a set of variable "N" bases (e.g., one or more variable "N" bases, etc.), where each "N" base is selected (e.g., randomly selected; selected according to predetermined statistical distributions and/or probabilities; etc.) from any one of an "A" base, a "G" base, a "T" base, and a "C" base. In a variation, an EMI region can include a synthesized region (e.g., on a microarray; using silicon-based synthesis; etc.) including one or more specified bases (e.g., designed and synthesized bases; etc.), such as synthesized regions designed to facilitate QCT sequence read cluster determination (e.g., by maximizing pairwise hamming distance between EMI regions; etc.). In variations, a QCT molecule can additionally or alternatively include a plurality of EMI regions (e.g., a variation region including a plurality of EMI regions; adjacent EMI regions; separated EMI regions; EMI regions including variable "N" bases; EMI regions including synthesized regions; etc.). For example, each variation region of the set of QCT molecules can include an embedded molecular identifier region including a set of variable "N" bases, where each "N" base is selected from any one of an "A" base, a "G" base, a "T" base, and a "C" base, where each QCT molecule of the set of QCT molecules further includes an additional EMI region including an additional set of variable "N" bases, where the additional EMI region is separated from the EMI region by a sequence region of the QCT molecule, such as where the set of variable "N" bases and the additional set of variable "N" bases can each include a determined (e.g., predetermined) number of "N" bases (e.g., greater than three "N" bases, greater than any suitable number of "N" bases, an exact number of "N" bases; etc.), and where determining a sequencing-related parameter (e.g., contamination parameter) can be based on QCT sequence read clusters derived based on the EMI regions and the additional EMI regions of the set of QCT molecules (e.g., based on distinct EMI sequence reads corresponding to pairs of an EMI region and an additional EMI region; etc.). In a variation, a variation region can additionally or alternatively include a synthesized In variations, as shown in FIG. 2, a QCT molecule can include a QCT identifier region identifying the QCT molecule (and/or other suitable QCT molecules), such as a shared QCT identifier region (e.g., a shared sequence region, with dissimilarity to one or more sequence regions of the target molecules, etc.) identifying QCT molecules belong to a set of QCT molecules (e.g., where different QCT identifier regions are unique to different sets of QCT molecules, etc.). In an example, the variation region of the each QCT molecule of a first set of QCT molecules can include a first EMI region separated from a second EMI region by at least a first QCT identifier region, where each additional QCT molecule of a second set of QCT molecules can include a first additional EMI region separated from a second additional EMI region by at least a second QCT identifier region. In an example, the first, the second, the first additional, and the second additional EMI regions can include a set of variable "N" bases, and where each "N" base is selected from any one of an "A" base, a "G" base, a "T" base, and a "C" base, and where computationally determining the set of QCT sequence read clusters can include determining the set of QCT sequence read clusters based on the first and the second QCT identifier regions, and on the first, the second, the first additional, and the second additional EMI regions. In an example, for the each QCT molecule of the first set of QCT molecules, the corresponding QCT molecule sequence is characterized by full sequence similarity to a first sequence template of the biological target except for the first QCT identifier region, the first EMI region, and the second EMI region; and where, for the each additional QCT molecule of the second set of QCT molecules, the corresponding additional QCT molecule sequence is characterized by full sequence similarity to a second sequence template except for the second QCT identifier region, the first additional EMI region, and the second additional EMI region. In a specific example, QCT molecule sequences can be identical to the target molecule sequence (e.g., one or more regions of the target molecule sequence; etc.), except for two separate sections of 5N sequences interrupted by a distinct, previously determined QCT identifier region (e.g., unique identifier sequence; etc.). In a specific example, QCT identifier regions (e.g., unique QCT ID sequence, as shown in FIG. 2, etc.), can be used to enable the use of multiple QCT libraries that can be added at one stage for internal control or at different stages for tracking of loss of input biological targets or other user errors. Additionally or alternatively, QCT identifier regions can be configured in any suitable manner. However, QCT molecules can include any suitable combination of any suitable type of regions (e.g., where different QCT molecules include the same or different types of and/or number of regions; with any suitable sequence similarity and/or dissimilarity to sequence regions of target molecules; etc.).

In variations, the method 100 can additionally or alternatively include generating one or more QCT libraries (e.g., each QCT library including QCT molecules, etc.) such as where a QCT library can include multiple sets of QCT molecules such as where each set of QCT molecules is identifiable by a different QCT identifier region. In an example, generating a QCT library can include amplifying different sets of QCT molecules (e.g., for preparation for sequencing, such as where the QCT molecules are amplified prior to addition to one or more components of a sample to generate a QCT mixture; etc.). In examples, generating a QCT library can include determining a number of QCT molecules to include in the QCT library. In a specific example, the solutions to the birthday problem can be used to determine the maximum number of unique QCT molecules that should be included in each sample given a particular diversity of QCT molecules, such as where, for $4^{10}$ sequences, which can be generated by 10 variable N bases in a QCT molecule, up to 1200 QCT molecules can be used with probability of ~0.5 of a single valid EMI collision ($\exp(-1200*1199/2/4^{10})$~0.5), and where at 200 QCT molecules, the probability of a single valid collision is ~2%. In a specific example, generating a QCT library can include generating a QCT library adapted for deployment (e.g., at a single stage of the at least one of the sequencing library preparation and the high throughput sequencing, etc.) of less than 0.00001 nanograms (and/or other suitable amounts) of amplifiable QCT molecules for each sample of a set of samples. However, determining the number of QCT molecules to include in a QCT library, and generating QCT libraries, can be performed in any suitable manner.

In an example, the QCT libraries can be generated by synthesizing complementary strand to single-stranded oligonucleotide sequences that contain variable "N" sequences. In a specific example, double stranded QCT libraries can be generated by re-suspending and annealing the QCT ultramers with a complementary primer sequence, extending the sequences using Klenow Fragment (exo-), and treating with Exonuclease I. The final product can be purified to remove unused single stranded DNA molecules, and QCT libraries can be quantified using fluorometric assays such as Qubit HS assay, from which the number of QCT molecules to be added to each sample can be calculated by using the expected molecular weight of the double-stranded QCT molecules.

However, generating QCT molecules S110 can be performed in any suitable manner.

2.2 Determining a Set of QCT Sequence Read Clusters.

Embodiments of the method 100 can include determining one or more QCT sequence read clusters S120, which can function to cluster QCT molecule sequence reads (e.g., after sequencing library preparation and sequencing, etc.) for facilitating sequencing-related parameter determination.

QCT sequence read clusters preferably include QCT molecule sequence reads (e.g., derived from the sequencing corresponding to one or more QCT mixtures generated based on one or more sets of QCT molecules and one or more samples including the biological target; etc.), but can additionally or alternatively include any suitable reads and/or components associated with sequencing.

QCT molecule sequence reads can be computationally clustered, such as for determining the identity of the one or more sets of QCT molecules that have been dispensed into each sample. Various computational clustering approaches can be used, including but not limited to Principle Component Analysis, K means, hierarchical clustering, and/or any sequence-identity-based clustering approaches. Additionally or alternatively, clustering, computational analyses associated with clustering (e.g., pre-processing, filtering, etc.), and/or any other suitable portions of embodiments of the method 100 can apply artificial intelligence approaches (e.g., machine learning approaches, etc.) including any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naive Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

Determining QCT sequence read clusters is preferably based on one or more regions (e.g., variation regions; QCT identifier regions; etc.) of the QCT molecules (e.g., based on sequence reads corresponding to the regions of the QCT molecules; etc.), but can additionally or alternatively be based on any suitable data. In a specific example, after QCT molecules (e.g., target-associated quality control templates, etc.) are combined with components of the sample, and the biological target (e.g., nucleic acid molecules including the target sequence region; etc.) is amplified using primers complementary to both the target sequence region and the QCT molecule sequence (e.g., target-associated regions of the QCT molecules; etc.), the molecules can be indexed for multiplexing, sequenced, and the sequencing reads can be separated based on their multiplexing indexes. In a specific example, indexed reads can then be clustered into different QCT groups by QCT identifier regions (e.g., QCT ID sequences; etc.) or can be identified based on exact sequence matches to the expected QCT sequences (except for variation regions such as the EMI region, etc.). In an example, determining (e.g., computationally, etc.) a set of QCT sequence read clusters can include clustering a first QCT molecule sequence read and a second QCT molecule sequence read into a QCT sequence read cluster, of the set of QCT sequence read clusters, based on a variation region sequence similarity (e.g., between a first variation region of the first QCT molecule, and a second variation region of the second QCT molecule; etc.) satisfying a first condition (e.g., fewer than a threshold number of bases of dissimilarity; etc.), and for each QCT sequence read cluster of the set of QCT sequence read clusters, determining an assignment of the QCT sequence read cluster to a sample identifier (e.g., to a sample, to a sample compartment associated with the sequencing library preparation and/or sequencing, etc.) of a set of sample identifiers identifying the set of samples, such as where determining the sequencing-related parameter (e.g., contamination parameter, etc.) can be based on the set of QCT sequence read clusters and the assignments of the QCT sequence read clusters to the sample identifiers of the set of sample identifiers. In a specific example, clustering the first and the second QCT sequence reads can include clustering the first and the second QCT sequence reads into the QCT sequence read cluster based on the variation region sequence similarity of fewer than three point substitutions, and based on a read depth associated with the QCT sequence read cluster satisfying a second condition (e.g., greater than 20 read depth per QCT sequence read cluster; greater than 30 read depth; greater than any suitable read depth; etc.). In a specific example, a QCT molecule sequence read (e.g., a sequence read including an EMI region sequence) can be aggregated if another QCT molecule sequence read with 2 or fewer point substitutions is observed in the same well at higher read depth. In a specific example, each EMI is assigned to a particular sample and corresponding well and index or index pairs.

In variations, determining QCT sequence read clusters can include determining and/or discarding (e.g., filtering out, etc.) non-valid QCT sequence read clusters (e.g., non-valid EMI clusters, etc.). In an example, as shown in FIG. 10, non-valid QCT sequence read clusters can include QCT sequence read clusters with read depth below and/or at a threshold (e.g., 20 or fewer reads; 30 or fewer reads; a threshold of any suitable read depth; etc.), and/or satisfying any suitable conditions (e.g., a number of reads matching predetermined read depth conditions; etc.), such as where the non-valid QCT sequence read clusters can be discarded for molecule counting. In a specific example, valid QCT sequence read clusters (e.g., remaining QCT sequence reader clusters after the discarding of non-valid QCT sequence read clusters, etc.) can be used to determine the ratio of quality control template number to sequencing read count for each sample (e.g., where the ratio can be used as a correction factor to quantify the number of target molecules, etc.). In a specific example, as shown in FIG. 10, at an average EMI read depth of >30, valid versus non-valid QCT sequence read clusters (e.g., EMI clusters, etc.) can clearly identified by a marked decrease in sequencing depth, and at lower average read-depths, adaptive approaches (e.g., adaptive read depth threshold determination; etc.) can be used to identify valid versus non-valid EMIs. In a specific example, determining a set of QCT sequence read clusters can include determining a filtered subset of QCT sequence read clusters (e.g., valid QCT sequence read clusters, etc.) based on read depths (e.g., satisfying a read depth threshold conditions and/or other suitable conditions; etc.) corresponding to the filtered subset of QCT sequence read clusters, such as where determining a sequencing-related parameter (e.g., target molecule count, such as of the number of target molecules present in the original sample; etc.) can include determining a QCT molecule count based on the filtered subset of QCT sequence read clusters (e.g., where the number of QCT sequence read clusters in the filtered subset of QCT sequence read clusters can correspond to the QCT molecule count; etc.); determining a correction factor ratio based on the QCT molecule count and the QCT molecule sequence reads (e.g., dividing the QCT molecule count by the QCT molecule sequence reads; etc.); and determining the target molecule count based on the correction factor ratio and target molecule sequence reads derived from the sequencing (e.g., multiplying the number of target molecule sequence reads by the correction factor ratio; etc.), the target molecule sequence reads associated with the biological target (e.g., including the target sequence region of the target molecule; etc.). In a specific example, the method 100 can include adaptively determining a read depth threshold based on read depth distribution features for the QCT molecule sequence reads, and where determining the filtered subset of QCT sequence read clusters can include determining the filtered subset based on the satisfaction of the adaptively determined read depth threshold by the read depths. In a specific example, each read depth of the read depths can correspond to greater than twenty reads (and/or other suitable number of reads; etc.) for the corresponding QCT sequence read cluster of the filtered subset of QCT sequence read clusters. In examples, due to sequencing and PCR errors, non-valid QCT sequence read clusters can be non-valid due to aspects other than contamination. Additionally or alternatively, determining valid or non-valid QCT sequence read clusters can be performed in any suitable manner. However, determining QCT sequence read clusters S120 can be performed in any suitable manner.

2.3 Determining a Sequencing-Related Parameter.

Embodiments of the method 100 can include determining one or more sequencing-related parameters S130.

Figure 11:
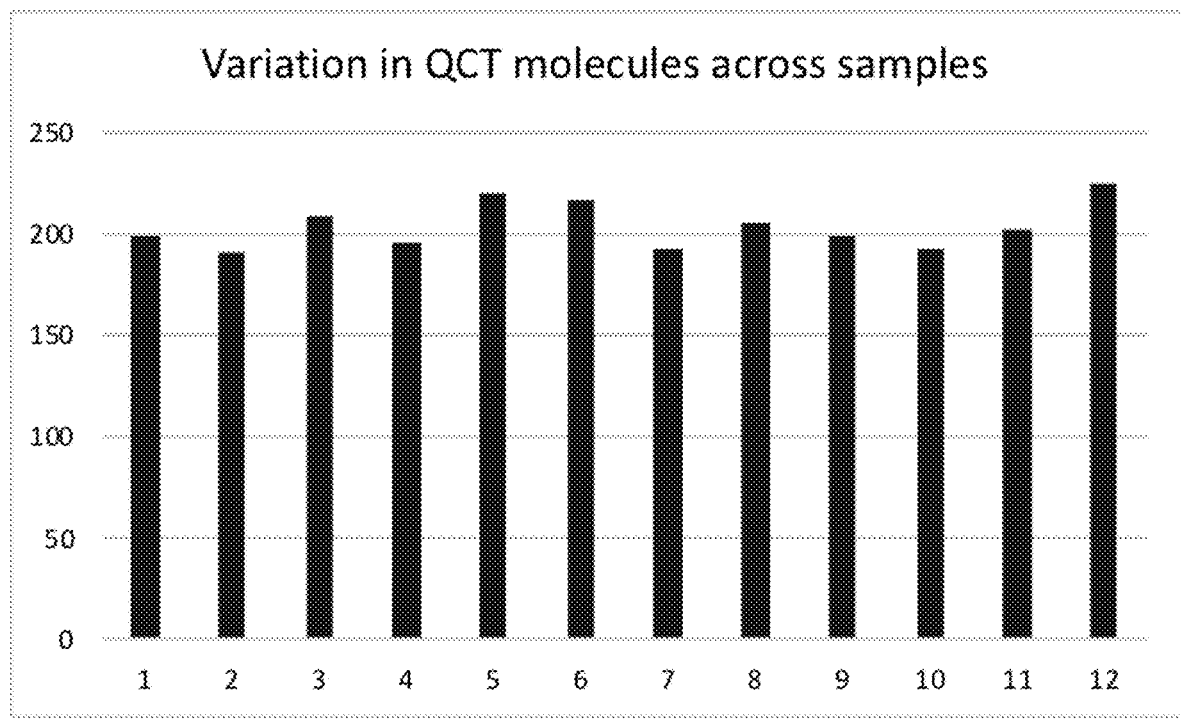
FIG. 11 includes a specific example of using QCT molecules with a plurality of samples to determine sample processing errors.

Sequencing-related parameters can include any one or more of: contamination parameters (e.g., describing contamination associated with sequencing library preparation and/or sequencing, such as across different users, samples, experiments, etc.); molecule count parameters (e.g., describing a number of molecules, such as target molecules and/or QCT molecules, initially present in a given sample and/or mixture; etc.); sample tracking parameters (e.g., associated with loss-of-sample; etc.); sample processing error parameters (e.g., describing noise; erroneous sample processing operations such as pipette error; systematic errors; etc.); quantification error parameters (e.g., describing quantification errors; etc.); analysis error parameters (e.g., describing computational analysis errors; etc.); and/or any suitable parameters associated with sequencing library preparation, sequencing, association analysis, and/or other suitable aspects. In an example, as shown in FIG. 11, numbers of QCT molecules determined across a plurality of samples can be used to determine sample processing errors describing noise and/or erroneous sample processing; where the same volume of QCT molecules, approximately corresponding to ~200 unique QCT molecules, can be added to each sample before PCR, and valid QCT sequence read clusters (e.g., EMI clusters, etc.) can be determined from sequencing data post-PCR and sequencing; where expected coefficient of variation (CV) for ~200 QCT molecules is sqrt(200)/200~7%, which is consistent with the observed data shown in FIG. 11 across the 12 samples; where if any samples drop below a certain threshold (e.g., 3 sigmas, 200-3*sqrt(200) ~150 or a less stringent threshold of ~200/2~100), the result can be used to identify sample processing error for that particular sample; and where the number of QCT molecules can also be increased to determine additional sample processing error parameters corresponding to below 7% CV in a process. In an example, determining the sequencing-related parameter can include identifying QCT sequence reads that are not assigned to a QCT sequence read cluster of the set of QCT sequence read clusters; and determining at least one of a sequencing error rate and a polymerase error rate (e.g., end-to-end sequencing and polymerase error rates; etc.) from a number of the QCT sequence reads that are not assigned and a total number of QCT sequence reads. In specific examples, any sequences that have variable regions (e.g., target variation regions, reference variation regions, etc.) to target or reference sequences but are not identical in sequence to a QCT read cluster sequence are due to sequence or polymerase errors. In a specific example, the read counts of these sequences, divided by total QCT read counts, is the combined sequencing and polymerase error frequency. The former, sequencing errors, can be produced by a linear process whereas polymerase errors can be produced by an exponential process (e.g., unless linear PCR is employed), wherein the effect of an error in an earlier cycle of PCR can be exponentially amplified. Thus, in a specific example, by analyzing the distribution of read counts of sequences that are not assigned to QCT read clusters, the contribution of sequencing versus polymerase errors can be calculated. However, determining sequencing error rates and/or polymerase error rates can be performed in any suitable manner.

In variations, determining sequencing-related parameters can be based on processing with a plurality of sets of QCT molecules (e.g., different sets of QCT molecules identified by different shared QCT identifier regions; different sets of QCT molecules deployed at different stages associated with the sequencing library preparation and/or sequencing; etc.), such as based on different subsets of QCT sequence read clusters corresponding to the different sets of QCT molecules. In an example, the method 100 can include generating a set of QCT molecules, each QCT molecule a first QCT identifier region shared amongst the set of QCT molecules and adapted to identifying the QCT molecule; generating a set of additional QCT molecules, each additional QCT molecule including a second QCT identifier region shared amongst the set of additional QCT molecules and adapted to identifying the additional QCT molecule; determining the set of QCT sequence read clusters based on the first and the second QCT identifier regions; and determining the sequencing-related parameter based on the set of QCT sequence read clusters. In a specific example, the set of QCT molecules can be adapted for deployment at a first stage of at least one of the sequencing library preparation and the sequencing, where the set of additional QCT molecules is adapted for deployment at a second stage of the at least one of the sequencing library preparation and the sequencing, where computationally determining the set of QCT sequence read clusters includes: determining a first subset of the set of QCT sequence read clusters (e.g., based on the first QCT identifier region and first variation regions of the corresponding first QCT molecules; etc.), where the first subset corresponds to the first QCT identifier region and is associated with the first stage; and determining a second subset of the set of QCT sequence read clusters (e.g., based on the second QCT identifier region and second variation regions of the corresponding second QCT molecules; etc.), where the second subset corresponds to the second QCT identifier region and is associated with the second stage; and where determining the sequencing-related parameter includes determining a sample tracking parameter associated with loss-of-sample, based on the first and the second subsets of the set of QCT sequence read clusters.

In an example, determining a sequencing-related parameter can include determining a first absolute count and a second absolute count corresponding to the set of QCT molecules and the set of additional QCT molecules, respectively, based on the set of QCT sequence read clusters, and determining at least one of a pipette error parameter and a quantification error parameter based on the first and the second absolute counts.

Figure 12:
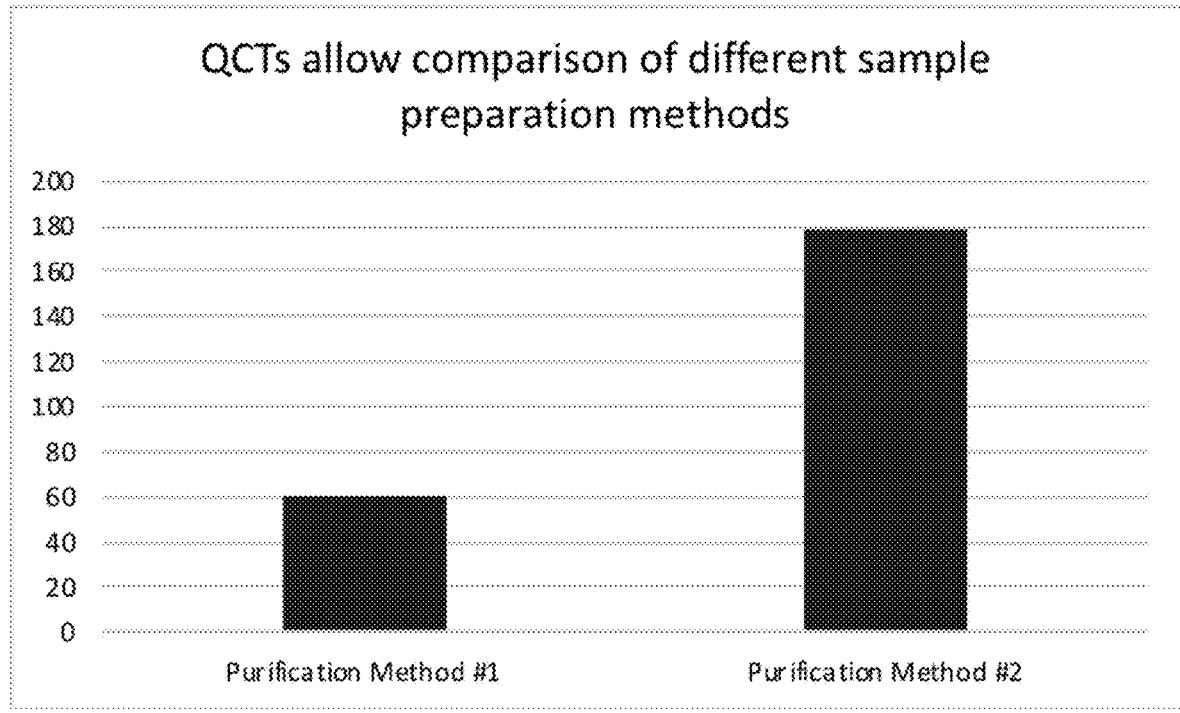
FIG. 12 includes a specific example of using QCT molecules at different stages.

In a specific example, as shown in FIG. 12, use of QCT molecules at different stages can allow comparison of different sample preparation approaches; such as where DNA purification approaches can be evaluated by addition of 200 QCT1 molecules (and/or any suitable number of QCT molecules) to each plasma sample before DNA purification; where DNA were purified from plasma by Purification Method #1 or Purification Method #2, and the resulting DNA samples were PCR-amplified and sequenced; where 200 QCT2 molecules (and/or any suitable number of QCT molecules) were added after DNA purification but before PCR-amplification; where the number of valid QCT sequence read clusters corresponding to QCT2 molecules was similar across two samples (within ~25%), indicating that the processing after purification was not different for these two samples; and where there was ~3× less valid QCT sequence read clusters for QCT1 for Purification Method #1, indicating that Purification Method #1 results in a significant loss-of-sample (e.g., of cfDNA).

However, determining sequencing-related parameters S130 can be performed in any suitable manner.

2.3.A Determining a Contamination Parameter.

Determining sequencing-related parameters S130 can additionally or alternatively include determining one or more contamination parameters S132. Contamination parameters can include one or more of a cross-contamination parameter (e.g., describing cross-contamination across samples and/or sample compartments associated with at least one of the sequencing library preparation and sequencing; cross-contamination across different users; etc.), a carry-over contamination parameter (e.g., describing carry-over contamination across a plurality of instances of the at least one of the sequencing library preparation and the sequencing; etc.), an index-hopping contamination parameter (e.g., describing index-hopping contamination associated with index-hopping primers, etc.). Contamination parameters can describe a degree of index misassignment (e.g., associated with the high throughput sequencing, etc.), such as where a contamination parameter can describe both (e.g., a cumulative effect of) cross-contamination (and/or other suitable contamination) and index misassignment, and/or any other suitable characteristics associated with sequencing library preparation and/or sequencing.

In an example, determining a contamination parameter can include determining a total contaminating percentage or fraction for a particular sample based on summing read-depths for contaminating sequences (e.g., found to be associated with the particular sample; found at a sample compartment corresponding to the sample; etc.) and dividing by a total number of reads (or total number of QCT molecule sequence reads associated with valid QCT sequence read clusters). In a specific example, as shown in FIG. 10, contamination parameters can be determined, where if the sequence of a non-valid EMI cluster for sequencing of Sample A is found as a valid EMI cluster at another sample (Sample B), it indicates that this read in Sample A is due to contamination from Sample B; where, by finding and summing the read depths for all such contaminating sequences and dividing by total number of reads (or total number of reads that map to valid EMI clusters), a total contaminating percentage or fraction for a particular sample can be determined; and where the total contaminating percentage or fraction can be used in the analysis of the maximum level of analytical sensitivity and specificity that the clinical assay can report, and/or as a threshold to report a failed assay and/or no-call result instead of a false positive; such as where, if a particular assay requires the detection of 0.1% allele fractions, a total contamination fraction at, above, or close to 0.1% for that sample can be used to identify a no-call result; and where, alternatively, the knowledge of the allele fractions from the contaminating samples can be used to adapt this threshold (i.e., for the measurement of a particular allele in a given sample, a 1% contamination from another sample that has 10% for the same allele has the same effect as 10% contamination from a sample that has that allele at 1%).

In a specific example, as shown in FIGS. 4A-4D, the contamination can be measured by identifying the source and destination of QCT molecule sequence reads (e.g., EMI sequence reads, etc.) in each sample compartment (e.g., well, etc.). In a specific example, if the same QCT molecule sequence read (e.g., the same EMI sequence read) is observed in a plurality of sample compartments (e.g., plurality of wells, etc.), the QCT molecule sequence read can be marked as originating from the sample compartment, of the plurality of sample compartments, with largest read depth and can be considered to be a contaminant in the other sample compartments of the plurality of sample compartments (e.g., the other well(s); etc.). In a specific example, determining a contamination parameter can include identifying a first and a second QCT sequence read cluster corresponding to a shared variation region sequence, where the assignments of the first and the second QCT sequence read clusters are to distinct sample identifiers (e.g., identifying distinct sample compartments; distinct samples; etc.) of the set of sample identifiers; generating a read depth comparison between a first read depth associated with the first QCT sequence read cluster and a second read depth associated with the second QCT sequence read cluster; and based on the read depth comparison, determining the contamination parameter associated with a sample identified by a distinct sample identifier of the distinct sample identifiers.

In an example, determining a contamination parameter can include determining a first molecular fingerprint associated with first amplification in a first instance of the sequencing library preparation, based on a set of QCT sequence read clusters; determining a second molecular fingerprint associated with second amplification in a second instance of the sequencing library preparation, based on an additional set of QCT sequence read clusters; and based on a comparison between the first and the second molecular fingerprints, determining a carry-over contamination parameter describing carry-over contamination from the first instance to the second instance.

Figure 13A:
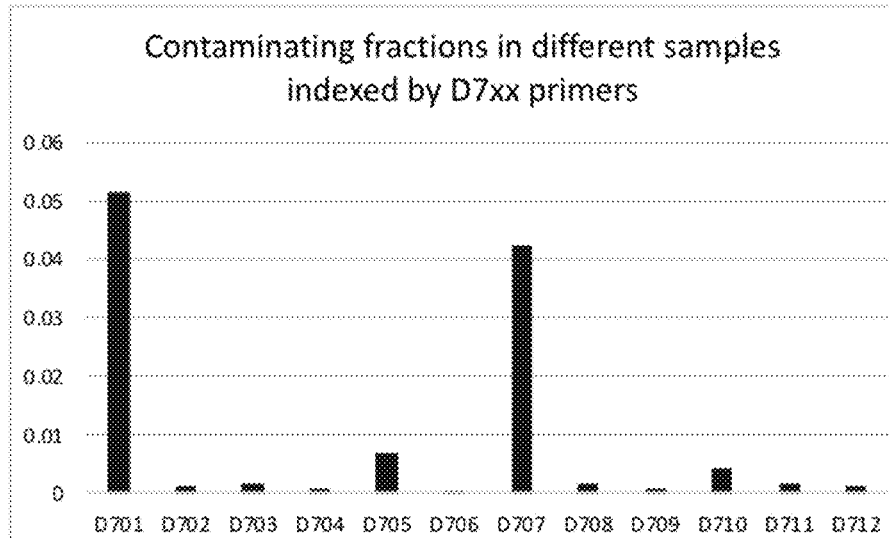
FIGS. 13A-13B include specific examples of characterization associated with index hopping.
Figure 13B:
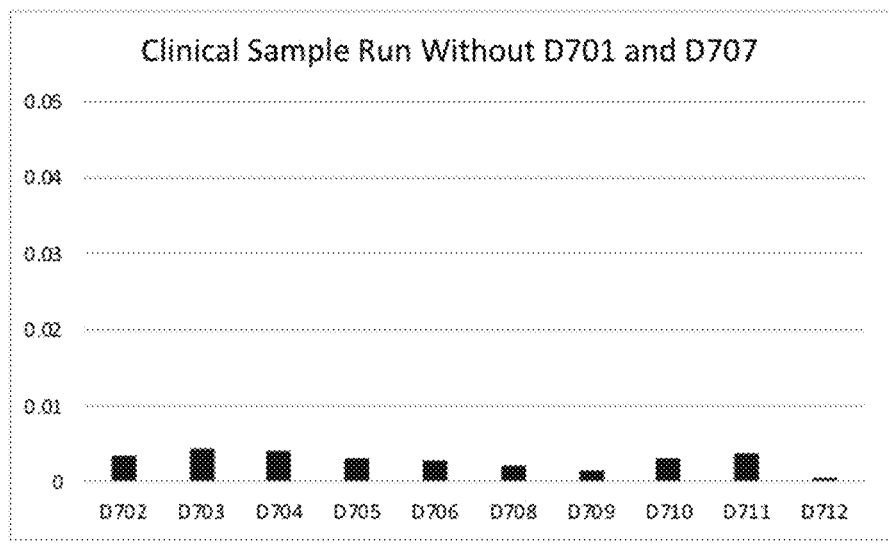

In a variation, determining a contamination parameter can include determining an index-hopping contamination parameters. In a specific example, as shown in FIGS. 13A-13B, QCT molecules can be used to facilitate identification and removal of contaminating and/or index-hopping primers; where, as shown in FIG. 13A, each sample was barcoded by a corresponding D7xx indexing primer and run on the same sequencing flow cell lane for a validation experiment; where D701 and D707 were found to have high contaminating fractions that originate from each other, potentially be due to the D701 and D707 indexing oligos being synthesized on the same oligo synthesis column, synthesis error, or index hopping, and where the level is significant at 5% and can affect clinical outcomes; and where, as shown in FIG. 13B, in subsequent runs with clinical samples, the indexing primers were not used, which decreased maximum contamination level to below 1%.

Figure 14:
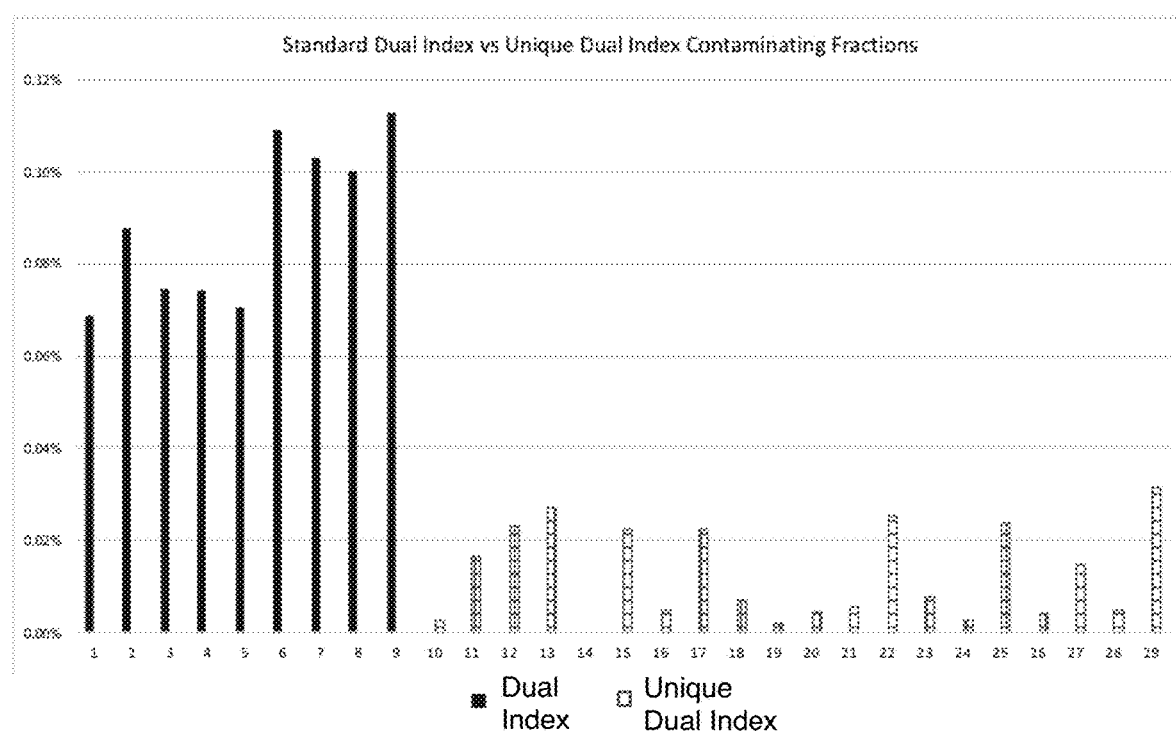
FIG. 14, includes a specific example for facilitating measurement of true contamination levels associated with use of unique dual index primers.

In a specific example, as shown in FIG. 14, QCT molecules can be used to facilitate measurement of true contamination levels associated with use of unique dual index primers; where standard dual indexing primers can result in 0.1% contamination (as shown by Samples 1 through 9), due to a combination of true sample-to-sample contamination, index hopping, and/or indexing oligo contamination; where unique dual indexing is expected to decrease the effect of index hopping and indexing oligo contamination to $0.001*0.001\sim1\text{-}6$; but where measurements indicate up to 0.03% (3e-5) contaminating fractions in dual unique-indexed reactions (as shown by Samples 10 through 29), which is higher than the expected 1e-6 contamination, which can indicate the detection of the true contamination levels under the laboratory conditions for the given assay.

However, determining contamination parameters S132 can be performed in any suitable manner.

2.3.B Determining a Molecule Count Parameter.

Determining sequencing-related parameters S130 can additionally or alternatively include determining one or more molecule count parameters S134. Molecule count parameters can include one or more of target molecule counts (e.g., absolute molecule count of target molecules, such as in the original sample; absolute count of endogenous target molecules, such as in the original sample; etc.); reference molecule counts (e.g., absolute count of endogenous reference molecules; such as in the original sample; etc.); QCT molecule counts (e.g., corresponding to a number of valid QCT sequence read clusters; corresponding to a number of distinct QCT molecules added to components of the sample; etc.); associated ratios (e.g., correction factors; ratios between a molecule count and an associated number of sequence reads; etc.); and/or any other suitable parameters associated with molecule counts.

Molecule count parameters are preferably used in facilitating one or more diagnoses, but can additionally or alternatively be used for (e.g., as inputs for) any suitable portions of embodiments of the method 100.

In variations, determining a molecule count parameter (e.g., target molecule count; etc.) can be based on a correction factor ratio determined based on a QCT molecule count (e.g., corresponding to a number of QCT sequence read clusters, such as a number of valid QCT sequence read clusters; etc.) and QCT molecule sequence reads (e.g., a number of the QCT molecule sequence reads corresponding to the QCT sequence read clusters; etc.), such as by multiplying the number of target molecule sequence reads by the correction factor ratio. In a specific example, the number of valid non-contaminating QCT sequence read clusters (e.g., remaining QCT sequence read clusters after discarding the QCT sequence read clusters with 2 or fewer reads, and/or with any suitable number or fewer of reads; etc.) can indicate the QCT molecule count (e.g., the number of QCT molecules for a particular sample compartment; for a particular sample; for a particular sample identifier; etc.). In a specific example, by dividing the QCT molecule count by the sequencing reads resulting from the corresponding QCT molecules, the correction factor can be found, such as where the correction factor multiplied by the sequencing reads belonging to the target molecules (e.g., in the particular sample compartment; from the particular sample; associated with the particular sample identifier; etc.) would result a target molecule count (e.g., an absolute number of initial biological target molecules that were accessible by the assay for amplification; etc.). In an example, the average QCT sequencing depth used in determining the absolute count of the endogenous target molecules and the absolute count of endogenous reference molecules is determined separately from their corresponding QCTs.

Alternatively, in a variation of an embodiment, the read depth threshold for discarding QCT sequence read clusters (e.g., for determining molecule count parameters and/or suitable sequencing-related parameters; etc.) can be determined adaptively based on features of QCT molecule sequence read (e.g., EMI sequence read) depth distribution. For example, a threshold may be set for each indexed sample by computing the mean EMI read depth within each sample, computing the square-root of this mean read depth, and discarding QCT sequence read clusters with read depth below the square-root of the mean read depth. Additionally or alternatively, read depth thresholds for discarding QCT sequence read clusters can be computed in any suitable manner.

However, determining molecule count parameters S134 can be performed in any suitable manner.

2.4 Facilitating Diagnosis.

Embodiments of the method 100 can additionally or alternatively include facilitating diagnosis S140, which can function to aid, determine, provide, and/or otherwise facilitate one or more diagnoses for one or more conditions.

Facilitating one or more diagnoses can include any one or more of determining one or more diagnoses (e.g., based on one or more sequencing-related parameters; etc.); providing one or more diagnoses (e.g., to one or more users; to one or more care providers, such as for use by one or more care providers in providing medical diagnoses to patients; etc.); aiding one or more diagnoses (e.g., providing one or more sequencing-related parameters and/or other suitable parameters to one or more care providers and/or other suitable entities, for use in determining a diagnosis, such as in combination with other data; etc.); and/or any suitable processes associated with diagnoses. For example, aiding diagnosis can include providing a contamination parameter (e.g., to a user; to a care provider; etc.) adapted for use in determination of a diagnostic outcome for assays associated with at least one of noninvasive prenatal testing and liquid biopsies. In an example, determining a target molecule count (and/or suitable sequencing-related parameters, etc.) can include determining the target molecule count (and/or the suitable sequencing-related parameters, etc.) for facilitating diagnosis associated with at least one of noninvasive prenatal testing and liquid biopsies.

In variations, facilitating diagnosis can include facilitating prenatal diagnosis (e.g., associated with noninvasive prenatal testing; for associated genetic disorders and/or suitable conditions; etc.). In an example, facilitating diagnosis can include facilitating prenatal diagnosis of one or more genetic disorders (e.g., single gene disorders, chromosomal abnormalities, etc.) based on target molecule count parameter and a reference molecule count parameter (e.g., based on a comparison between an absolute count of endogenous target sequences and an absolute count of endogenous reference sequences; etc.).

In variations, facilitating diagnosis can include facilitating diagnosis of one or more single gene disorders (and/or suitable genetic disorders). For example, determining an absolute count of endogenous target molecules can include determining the absolute count of the endogenous target molecules including a mutation associated with the single gene disorder (e.g., based on dividing the total read count for the endogenous target molecules by an average QCT sequencing depth, such as derived by dividing a number of QCT molecule sequence reads by the unique number of QCT molecules; etc.), where determining an absolute count of the endogenous reference molecules can include determining the absolute count of the endogenous reference molecules lacking the mutation (e.g., based on dividing the total read count for the endogenous reference molecules by the average QCT sequencing depth, etc.); and facilitating prenatal diagnosis of the genetic disorder of the single gene disorder based on (e.g., a comparison between, etc.) the absolute count of endogenous target sequences and the absolute count of endogenous reference sequences. In specific examples, as shown in FIGS. 15A-15D, the number of disease and non-disease alleles can be measured and compared in a sample to determine the genotype of a developing fetus from maternal blood; where FIG. 15A includes the number of HbS (mutated hemoglobin) and HbA (normal hemoglobin) molecules as measured by QCT molecules in sickle cell trait (SCT) samples where HbS and HbA alleles are expected to be at the same frequency, representing cases where both the pregnant mother and the developing fetus are heterozygous for the disorder; where FIG. 15B includes the number of HbS and HbA molecules as measured by QCTs in SCT+10% sickle cell disease (SCD) samples, representing cases where the pregnant mother is a carrier for the disorder, and the developing fetus have inherited the disease allele from both parents and therefore have the disease; where FIG. 15C includes a number of molecules and fetal fraction measurement (e.g., measurement at up to 9 loci where mother and fetus differ in genotype) for use in calculate the posterior probability that the fetus has inherited the disorder by a relative mutation dosage (RMD) analysis; and where FIG. 15D includes the mean and 95% confidence intervals for 0% vs. 10% SCD addition to SCT sample (e.g., representing carrier vs. disease fetus from a pregnant mother who is a carrier for the disorder). However, facilitating diagnoses of single gene disorders can be performed in any suitable manner.

Figure 16A:
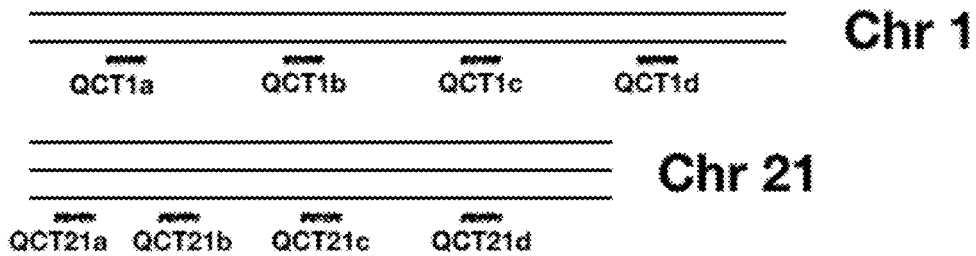
FIGS. 16A-16B include specific examples associated with facilitating diagnosis of a chromosomal abnormality.
Figure 16B:
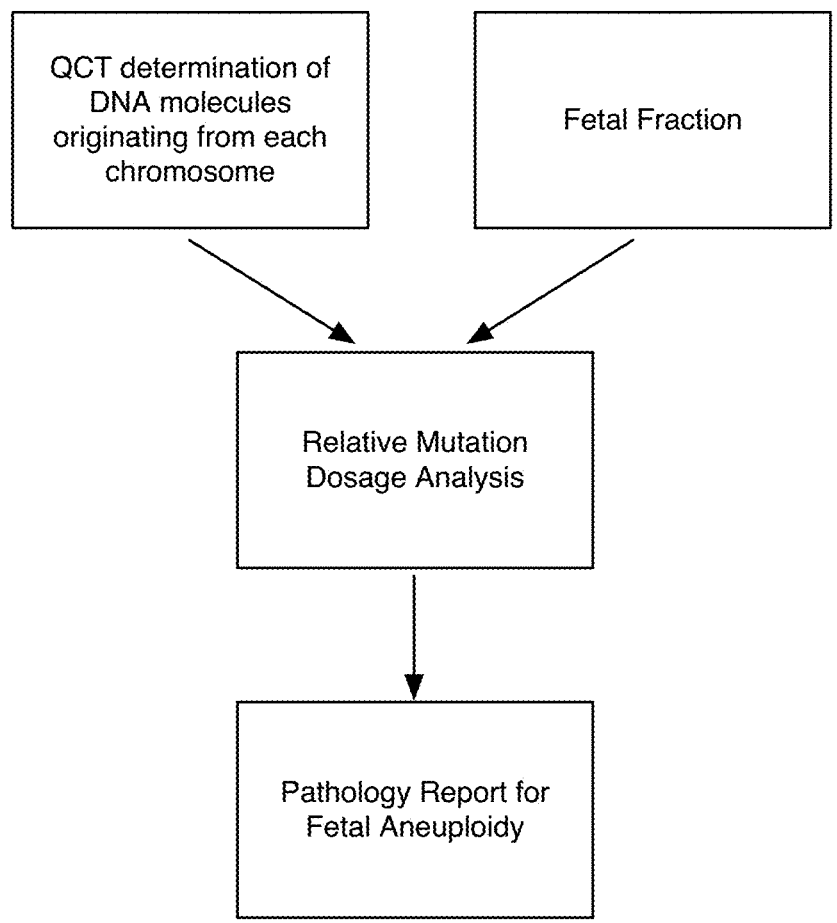

In variations, facilitating diagnosis can include facilitating diagnosis of one or more chromosomal abnormalities (and/or suitable genetic disorders). For example, determining the absolute count of the endogenous target molecules can include determining the absolute count of the endogenous target molecules associated with a first chromosome (e.g., based on dividing the total read count for the endogenous target molecules by the average QCT sequencing depth; etc.), where determining the absolute count of the endogenous reference molecules can include determining the absolute count of the endogenous reference molecules associated with a second chromosome (e.g., based on dividing the total read count for the endogenous reference molecules by the average QCT sequencing depth, etc.); and facilitating prenatal diagnosis of the chromosomal abnormality based on (e.g., a comparison between, etc.) the absolute count of endogenous target sequences and the absolute count of endogenous reference sequences. In specific examples, as shown in FIGS. 16A-16B, the number of Chr21 and another chromosome can be counted similarly using QCT molecules to determine if there is an excess number of Chr 21 (e.g., compared to another chromosome) to indicate the fetus has Down syndrome; where for a difference of 3 vs. 2 chromosomes being counted, the signal can be half of an inherited recessive disorder (e.g., HbSS vs HbAS is a signal of 2 vs 1; 100% increase vs. 50% increase), which can indicate a requirement of more than one locus on each chromosome to be counted for improved accuracy in measuring Down syndrome in the developing fetus from circulating DNA in maternal blood; and where portions of embodiments of the method 100 can additionally or alternatively be used to facilitate diagnoses for other de novo mutations and/or chromosomal abnormalities such as Trisomy 18 and/or DiGeorge Syndrome.

In variations, facilitating diagnosis can include facilitating diagnosis of one or more chromosomal microdeletions. For example, determining the absolute count of the endogenous target molecules can include determining the absolute count of the endogenous target molecules associated with a microdeletion region, based on dividing the total read count for the endogenous target molecules by the average QCT sequencing depth, where determining the absolute count of the endogenous reference molecules can include determining the absolute count of the endogenous reference molecules associated with a second chromosomal region not expected to have a microdeletion, based on dividing the total read count for the endogenous reference molecules by the average QCT sequencing depth, and where facilitating the diagnosis (e.g., the prenatal diagnosis, etc.) of the genetic disorder can include facilitating the diagnosis (e.g., prenatal diagnosis; etc.) of the chromosomal microdeletion based on the comparison.

In variations, facilitating diagnosis can include facilitating diagnosis of one or more copy number variations. For example, determining the absolute count of the endogenous target molecules can include determining the absolute count of the endogenous target molecules associated with a region that may have copy number variation, based on dividing the total read count for the endogenous target molecules by the average QCT sequencing depth, where determining the absolute count of the endogenous reference molecules can include determining the absolute count of the endogenous reference molecules associated with a region not expected to have a copy number variation, based on dividing the total read count for the endogenous reference molecules by the average QCT sequencing depth, and where facilitating the diagnosis (e.g., prenatal diagnosis) of the genetic disorder can include facilitating the diagnosis (e.g., prenatal diagnosis) of the copy number variation based on the comparison.

Additionally or alternatively, facilitating diagnoses can be for any suitable conditions.

Figure 15A:
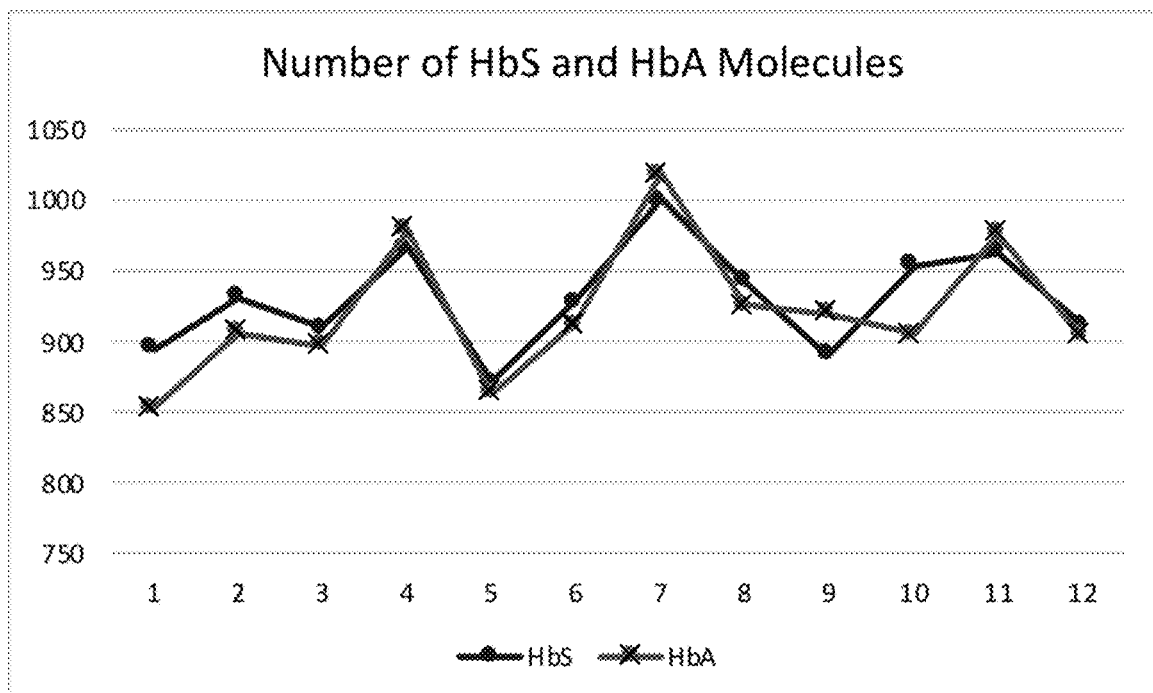
FIGS. 15A-15D include specific examples associated with facilitating diagnosis of a single gene disorder.
Figure 15B:
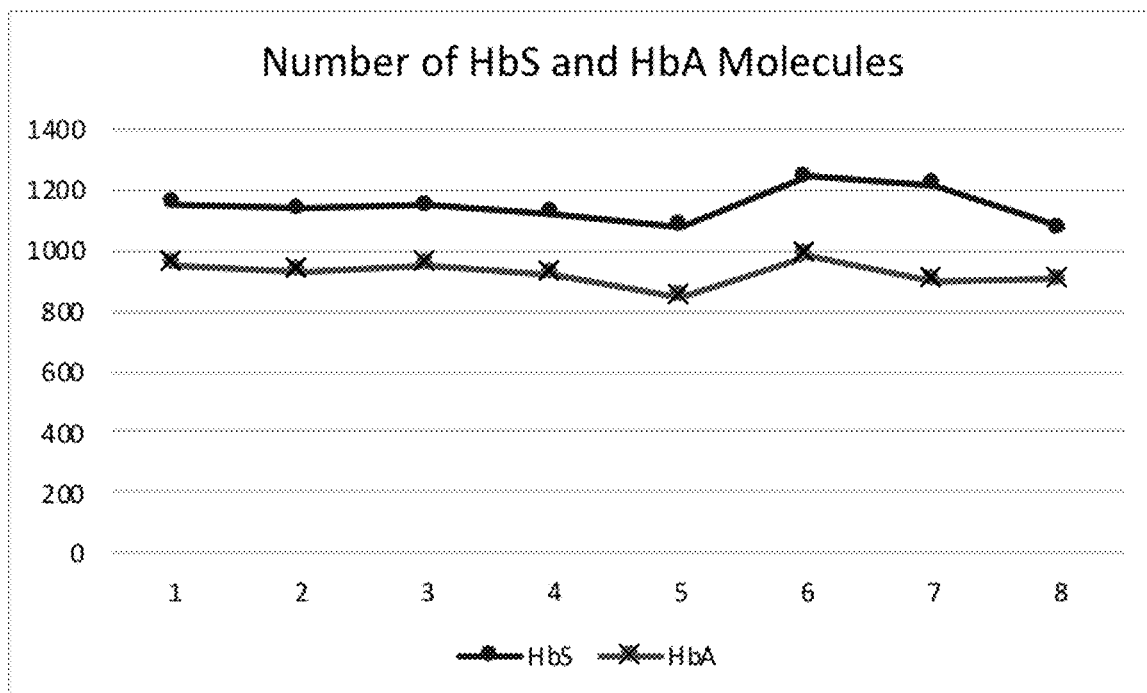
Figure 15C:
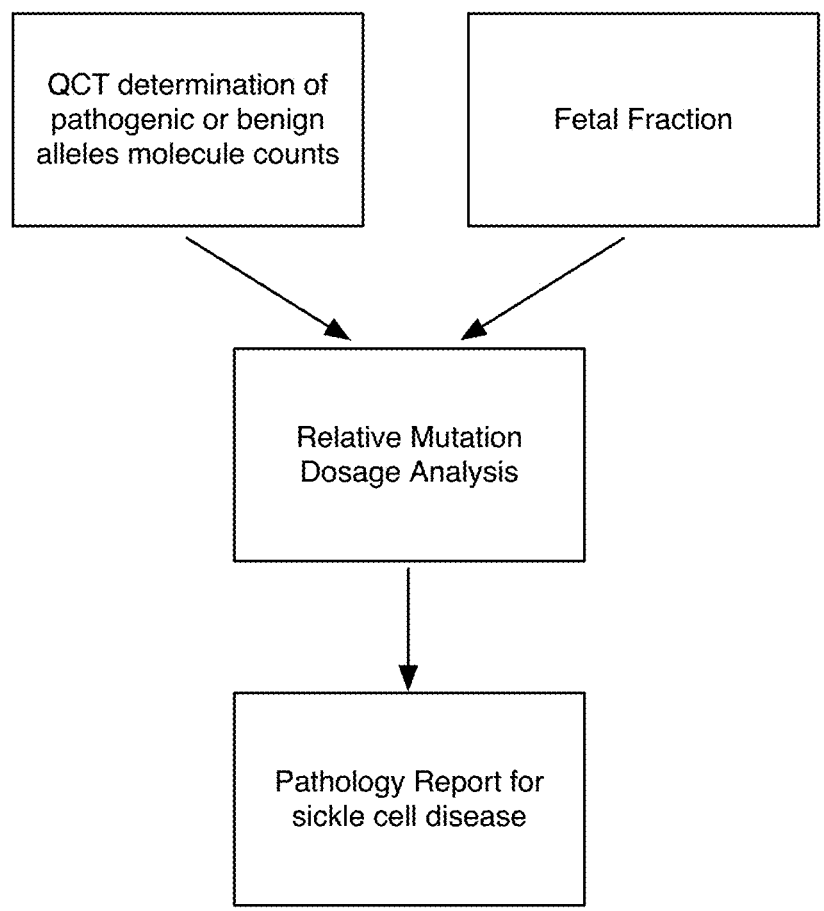
Figure 15D:
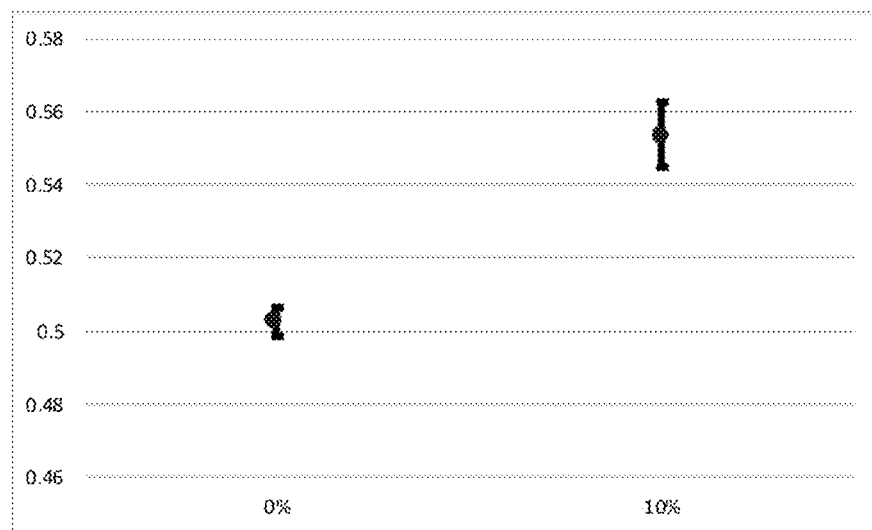

As shown in FIGS. 15C and 16B, facilitating diagnosis can be based on one or more fetal fraction measurements. For example facilitating the prenatal diagnosis can include facilitating the prenatal diagnosis of the genetic disorder based on a fetal fraction measurement, the absolute count of endogenous target sequences, and the absolute count of endogenous reference sequences. However, using fetal fraction measurements can be performed in any suitable manner for any suitable processes of embodiments of the method 100, and facilitating diagnosis S140 can be performed in any suitable manner.

However, embodiments of the method 100 can be performed in any suitable manner.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

We claim:

1. A method for characterization associated with at least one of sequencing library preparation and sequencing, the method comprising:
   generating a set of quality control template (QCT) molecules, each QCT molecule comprising:
      a target-associated region matching a target sequence region of a target molecule; and
      a variation region not matching a corresponding region of the target molecule, the variation region comprising an embedded molecular identifier having a randomly selected nucleotide sequence, wherein the embedded molecular identifier identifies the QCT molecule;
   generating a mixture comprising the set of QCT molecules and nucleic acid molecules of a sample;
   co-amplifying the mixture;
   sequencing the co-amplified mixture to generate sequencing data;
   computationally determining a set of QCT sequence read clusters, using the sequencing data, based on a number of distinct variation regions of the set of QCT molecules identified in the sequencing data;
   computationally determining a count of QCT molecules that were in the mixture prior to the co-amplification based on the set of QCT sequence read clusters; and based on the count of QCT molecules, determining a sequencing related parameter associated with the at least one of the sequencing library preparation and the sequencing.

2. The method of claim 1,
wherein the each QCT molecule comprises a first QCT identifier region shared amongst the set of QCT molecules and adapted to identifying the QCT molecule,
wherein the method further comprises generating a set of additional QCT molecules, each additional QCT molecule comprising a second QCT identifier region shared amongst the set of additional QCT molecules and adapted to identifying the additional QCT molecule; and
wherein computationally determining the set of QCT sequence read clusters comprises determining the set of QCT sequence read clusters based on the first and the second QCT identifier regions.

3. The method of claim 2,
wherein the set of QCT molecules is adapted for deployment at a first stage of the at least one of the sequencing library preparation and the sequencing,
wherein the set of additional QCT molecules is adapted for deployment at a second stage of the at least one of the sequencing library preparation and the sequencing,
wherein computationally determining the set of QCT sequence read clusters comprises:
  determining a first subset of the set of QCT sequence read clusters, wherein the first subset corresponds to the first QCT identifier region and is associated with the first stage, and
  determining a second subset of the set of QCT sequence read clusters, wherein the second subset corresponds to the second QCT identifier region and is associated with the second stage; and
  wherein determining the sequencing related parameter associated with the at least one of the sequencing library preparation and the sequencing comprises determining a sample tracking parameter associated with loss-of-sample, based on the first and the second subsets of the set of QCT sequence read clusters.

4. The method of claim 2, wherein determining the sequencing related parameter associated with the at least one of the sequencing library preparation and the sequencing comprises:
  determining a first absolute count and a second absolute count corresponding to the set of QCT molecules and the set of additional QCT molecules, respectively, based on the set of QCT sequence read clusters, and
  determining at least one of a pipette error parameter and a quantification error parameter based on the first and the second absolute counts.

5. The method of claim 2, wherein determining the sequencing related parameter associated with the at least one of the sequencing library preparation and the sequencing comprises:
  identifying QCT sequence reads that are not assigned to a QCT sequence read cluster of the set of QCT sequence read clusters; and
  determining at least one of a sequencing error rate and a polymerase error rate from a number of the QCT sequence reads that are not assigned and a total number of QCT sequence reads.

6. The method of claim 2,
wherein the variation region of the each QCT molecule comprises a first embedded molecular identifier (EMI) region separated from a second EMI region by at least the first QCT identifier region,
wherein the each additional QCT molecule comprises a first additional EMI region separated from a second additional EMI region by at least the second QCT identifier region,
wherein the first, the second, the first additional, and the second additional EMI regions comprise a set of variable "N" bases, and wherein each "N" base is selected from any one of an "A" base, a "G" base, a "T" base, and a "C" base, and
wherein computationally determining the set of QCT sequence read clusters comprises determining the set of QCT sequence read clusters based on the first and the second QCT identifier regions, and on the first, the second, the first additional, and the second additional EMI regions.

7. The method of claim 6,
wherein, for each QCT molecule, the corresponding QCT molecule sequence is characterized by full sequence similarity to a first sequence template of the target molecule except for the first QCT identifier region, the first EMI region, and the second EMI region;
wherein, for each additional QCT molecule, the corresponding additional QCT molecule sequence is characterized by full sequence similarity to a second sequence template except for the second QCT identifier region, the first additional EMI region, and the second additional EMI region.

8. The method of claim 1,
wherein determining the set of QCT sequence read clusters comprising determining a filtered subset of QCT sequence read clusters based on read depths corresponding to the filtered subset of QCT sequence read clusters,
wherein determining a target molecule count comprises:
  determining a QCT molecule count based on the filtered subset of QCT sequence read clusters;
  determining a correction factor ratio based on the QCT molecule count and the QCT molecule sequence reads; and
  determining the target molecule count based on the correction factor ratio and target molecule sequence reads derived from the sequencing, the target molecule sequence reads associated with the target molecule.

9. The method of claim 8, further comprising adaptively determining a read depth threshold based on read depth distribution features for the QCT molecule sequence reads, wherein determining the filtered subset of QCT sequence read clusters comprises determining the filtered subset based on the satisfaction of the adaptively determined read depth threshold by the read depths.

10. The method of claim 8, wherein each read depth of the read depths corresponds to greater than twenty reads for the corresponding QCT sequence read cluster of the filtered subset of QCT sequence read clusters.

11. The method of claim 8, wherein determining the target molecule count comprises determining the target molecule count for facilitating diagnosis associated with at least one of noninvasive prenatal testing and liquid biopsies.

12. The method of claim 1, wherein determining the sequencing related parameter associated with the at least one of the sequencing library preparation and the sequencing comprises determining a contamination parameter comprising at least one of: a cross-contamination parameter describing cross-contamination across sample compartments associated with the at least one of the sequencing library preparation and the sequencing, a carry-over contamination parameter describing carry-over contamination across a plurality of instances of the at least one of the sequencing library preparation and the sequencing, and an index-hopping contamination parameter describing index-hopping contamination associated with index-hopping primers.

13. The method of claim 12,
wherein the set of QCT molecules is adapted for the sequencing,
wherein generating the set of QCT molecules comprises:
amplifying a first subset of QCT molecules of the set of QCT molecules; and
amplifying a second subset of QCT molecules of the set of QCT molecules,
wherein the QCT molecule sequencing reads are derived from the sequencing corresponding to:
the QCT mixture generated based on the first subset of QCT molecules and the sample comprising the biological target, and
an additional QCT mixture generated based on the second subset of QCT molecules and an additional sample comprising the biological target, wherein the sample and the additional sample respectively correspond to a first sample compartment and a second sample compartment of the sample compartments.

14. The method of claim 1, wherein determining the sequencing related parameter associated with the at least one of the sequencing library preparation and the sequencing comprises calculating the average QCT sequencing depth based on dividing a number of the QCT molecule sequence reads by the unique number of QCT molecules.

15. The method of claim 1, wherein determining the sequencing related parameter associated with the at least one of the sequencing library preparation and the sequencing comprises determining an absolute count of the target molecules.

16. The method of claim 15, wherein determining the absolute count of the target molecules comprises dividing a total read count for the target molecules by the average QCT sequencing depth.

17. The method of claim 1, wherein determining the sequencing related parameter associated with the at least one of the sequencing library preparation and the sequencing comprises determining a target molecule count describing a number of molecules of the biological target associated with the sequencing, based on the count of QCT molecules.

* * * * *

UNITED STATES PATENT AND TRADEMARK OFFICE
CERTIFICATE OF CORRECTION

PATENT NO. : 11,629,381 B2
APPLICATION NO. : 16/056254
DATED : April 18, 2023
INVENTOR(S) : Tsao et al.

It is certified that error appears in the above-identified patent and that said Letters Patent is hereby corrected as shown below:

On the Title Page

Item (54), in Column 1, in "Title", Line 1, after "TEMPLATES" insert -- FOR --.

Item (56), in Column 2, under "Other Publications", Line 12, delete "dat." and insert -- dat, --, therefor.

In the Specification

In Column 1, Line 1, after "TEMPLATES" insert -- FOR --.

In the Claims

In Column 26, Claim 8, Line 32, delete "comprising" and insert -- comprises --, therefor.

In Column 28, Claim 14, Line 6, delete "the" and insert -- an --, therefor.

Signed and Sealed this
Fourteenth Day of November, 2023

Katherine Kelly Vidal
*Director of the United States Patent and Trademark Office*